United States Patent
Francischelli et al.

(10) Patent No.: US 8,162,933 B2
(45) Date of Patent: Apr. 24, 2012

(54) VIBRATION SENSITIVE ABLATION DEVICE AND METHOD

(75) Inventors: David E. Francischelli, Anoka, MN (US); Scott E. Jahns, Hudson, WI (US); James R. Keogh, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 1197 days.

(21) Appl. No.: 10/792,178

(22) Filed: Mar. 3, 2004

(65) Prior Publication Data

US 2004/0186465 A1    Sep. 23, 2004

Related U.S. Application Data

(63) Continuation of application No. 09/844,221, filed on Apr. 26, 2001, now abandoned, which is a continuation-in-part of application No. 09/559,604, filed on Apr. 27, 2000, now abandoned.

(51) Int. Cl.
*A61B 18/18* (2006.01)

(52) U.S. Cl. .......................................... 606/41; 128/898

(58) Field of Classification Search ................... 607/101, 607/102, 119, 122, 126–8; 601/6, 7; 600/387; 606/41, 42, 45–50, 9–34; 128/898
See application file for complete search history.

(56) References Cited

U.S. PATENT DOCUMENTS

| | | | |
|---|---|---|---|
| 3,736,936 A | 6/1973 | Basiulis et al. | |
| 3,807,403 A | 4/1974 | Stumpf et al. | |
| 3,823,575 A | 7/1974 | Parel | |
| 3,823,718 A | 7/1974 | Tromovitch | |
| 3,827,436 A | 8/1974 | Stumpf et al. | |
| 3,830,239 A | 8/1974 | Stumpf | |
| 3,859,986 A | 1/1975 | Okada et al. | |
| 3,862,627 A | 1/1975 | Hans, Sr. | |
| 3,886,945 A | 6/1975 | Stumpf et al. | |
| 3,907,339 A | 9/1975 | Stumpf et al. | |
| 3,910,277 A | 10/1975 | Zimmer | |
| 3,913,581 A | 10/1975 | Ritson et al. | |
| 3,924,628 A | 12/1975 | Droegemueller et al. | |
| 4,018,227 A | 4/1977 | Wallach | |
| 4,022,215 A | 5/1977 | Benson | |
| 4,061,135 A | 12/1977 | Widran et al. | |
| 4,063,560 A | 12/1977 | Thomas et al. | |
| 4,072,152 A | 2/1978 | Linehan | |
| 4,082,096 A | 4/1978 | Benson | |
| 4,207,897 A | 6/1980 | Lloyd et al. | |
| 4,248,224 A | 2/1981 | Jones | |

(Continued)

FOREIGN PATENT DOCUMENTS

GB    2 070 935 A    2/1981

(Continued)

OTHER PUBLICATIONS

Chitwood, "Will C. Sealy, MD: The Father of Arrhythmia Surgery—The Story of the Fisherman with a Fast Pulse," Annals of Thoracic Surgery 58:1228-1239, 1994.

(Continued)

*Primary Examiner* — Henry M Johnson, III

(57) ABSTRACT

An ablation apparatus including a maneuvering mechanism, a conductive element attached to the apparatus, a sensor attached to the apparatus and an output device in communication with the sensor is provided. The sensor senses vibration during the ablation procedure and sends a signal to the output device to reduce power to the conductive element.

9 Claims, 8 Drawing Sheets

U.S. PATENT DOCUMENTS

| | | | |
|---|---|---|---|
| 4,275,734 | A | 6/1981 | Mitchiner |
| 4,278,090 | A | 7/1981 | van Gerven |
| 4,377,168 | A | 3/1983 | Rzasa et al. |
| 4,519,389 | A | 5/1985 | Gudkin et al. |
| 4,598,698 | A | 7/1986 | Siegmund |
| 4,601,290 | A | 7/1986 | Effron et al. |
| 4,664,110 | A | 5/1987 | Schanzlin |
| 4,736,749 | A | 4/1988 | Lundback |
| 4,779,611 | A | 10/1988 | Grooters et al. |
| 4,802,475 | A | 2/1989 | Weshahy |
| 4,815,470 | A | 3/1989 | Curtis et al. |
| 4,872,346 | A | 10/1989 | Kelly-Fry et al. |
| 4,916,922 | A | 4/1990 | Mullens |
| 4,917,095 | A | 4/1990 | Fry et al. |
| 4,936,281 | A | 6/1990 | Stasz |
| 4,946,460 | A | 8/1990 | Merry et al. |
| 5,013,312 | A | 5/1991 | Parins et al. |
| 5,029,574 | A | 7/1991 | Shimamura et al. |
| 5,044,165 | A | 9/1991 | Linner et al. |
| 5,078,713 | A | 1/1992 | Varney |
| 5,080,102 | A | 1/1992 | Dory |
| 5,080,660 | A | 1/1992 | Buelina |
| 5,100,388 | A | 3/1992 | Behl et al. |
| 5,102,410 | A | 4/1992 | Dressel ............ 606/15 |
| 5,108,390 | A | 4/1992 | Potocky et al. |
| 5,147,355 | A | 9/1992 | Friedman et al. |
| 5,178,133 | A | 1/1993 | Pena |
| 5,188,111 | A | 2/1993 | Yates et al. ............ 128/657 |
| 5,194,723 | A * | 3/1993 | Cates et al. ............ 250/205 |
| 5,207,674 | A | 5/1993 | Hamilton |
| 5,217,860 | A | 6/1993 | Fahy et al. |
| 5,222,501 | A | 6/1993 | Ideker et al. |
| 5,224,943 | A | 7/1993 | Goddard |
| 5,228,923 | A | 7/1993 | Hed |
| 5,231,995 | A | 8/1993 | Desai |
| 5,232,516 | A | 8/1993 | Hed |
| 5,254,116 | A | 10/1993 | Baust et al. |
| 5,263,493 | A | 11/1993 | Avitall |
| 5,269,291 | A | 12/1993 | Carter |
| 5,275,595 | A | 1/1994 | Dobak, III |
| 5,277,201 | A | 1/1994 | Stern |
| 5,281,213 | A | 1/1994 | Milder et al. |
| 5,281,215 | A | 1/1994 | Milder |
| 5,295,484 | A | 3/1994 | Marcus et al. |
| 5,309,896 | A | 5/1994 | Moll et al. |
| 5,316,000 | A | 5/1994 | Chapelon et al. |
| 5,317,878 | A | 6/1994 | Bradshaw et al. |
| 5,318,525 | A | 6/1994 | West et al. |
| 5,322,520 | A | 6/1994 | Milder |
| 5,323,781 | A | 6/1994 | Ideker et al. |
| 5,324,255 | A | 6/1994 | Passafaro et al. |
| 5,324,284 | A | 6/1994 | Imran |
| 5,324,286 | A | 6/1994 | Fowler |
| 5,334,181 | A | 8/1994 | Rubinsky et al. |
| 5,334,193 | A * | 8/1994 | Nardella ............ 606/41 |
| 5,339,289 | A | 8/1994 | Erickson ............ 367/149 |
| 5,348,554 | A | 9/1994 | Imran et al. |
| 5,353,783 | A | 10/1994 | Nakao et al. |
| 5,354,258 | A | 10/1994 | Dory |
| 5,361,752 | A | 11/1994 | Moll et al. |
| 5,385,148 | A | 1/1995 | Lesh et al. |
| 5,396,887 | A | 3/1995 | Imran |
| 5,397,304 | A | 3/1995 | Truckai |
| 5,400,770 | A | 3/1995 | Nakao et al. |
| 5,400,783 | A | 3/1995 | Pomeranz et al. |
| 5,403,309 | A | 4/1995 | Coleman et al. |
| 5,403,311 | A | 4/1995 | Abele et al. |
| 5,405,376 | A | 4/1995 | Mulier et al. |
| 5,409,483 | A | 4/1995 | Campbell et al. |
| 5,423,807 | A | 6/1995 | Milder |
| 5,423,811 | A | 6/1995 | Imran et al. |
| 5,427,119 | A | 6/1995 | Swartz et al. |
| 5,431,649 | A | 7/1995 | Mulier et al. |
| 5,433,708 | A | 7/1995 | Nichols et al. |
| 5,435,308 | A | 7/1995 | Gallup et al. |
| 5,437,651 | A | 8/1995 | Todd et al. |
| 5,443,463 | A | 8/1995 | Stern et al. ............ 606/51 |
| 5,443,470 | A | 8/1995 | Stern et al. |
| 5,450,843 | A | 9/1995 | Moll et al. |
| 5,452,582 | A | 9/1995 | Longsworth |
| 5,452,733 | A | 9/1995 | Sterman et al. |
| 5,462,545 | A | 10/1995 | Wang et al. |
| 5,465,717 | A | 11/1995 | Imran et al. |
| 5,469,853 | A | 11/1995 | Law et al. |
| 5,472,876 | A | 12/1995 | Fahy |
| 5,478,309 | A | 12/1995 | Sweezer et al. |
| 5,478,330 | A | 12/1995 | Imran et al. |
| 5,486,193 | A | 1/1996 | Bourne et al. |
| 5,487,385 | A | 1/1996 | Avitall |
| 5,487,757 | A | 1/1996 | Truckai et al. |
| 5,496,312 | A | 3/1996 | Klicek |
| 5,497,774 | A | 3/1996 | Swartz et al. |
| 5,498,248 | A | 3/1996 | Milder |
| 5,500,012 | A | 3/1996 | Brucker et al. |
| 5,505,730 | A | 4/1996 | Edwards |
| 5,516,505 | A | 5/1996 | McDow |
| 5,520,682 | A | 5/1996 | Baust et al. |
| 5,522,870 | A | 6/1996 | Ben-Zion |
| 5,536,267 | A | 7/1996 | Edwards et al. |
| 5,545,195 | A | 8/1996 | Lennox et al. |
| 5,545,200 | A | 8/1996 | West et al. |
| 5,549,661 | A | 8/1996 | Kordis et al. |
| 5,555,883 | A | 9/1996 | Avitall |
| 5,558,671 | A | 9/1996 | Yates |
| 5,560,362 | A | 10/1996 | Sliwa, Jr. et al. |
| 5,562,720 | A | 10/1996 | Stern et al. |
| 5,569,241 | A | 10/1996 | Edwards |
| 5,571,088 | A | 11/1996 | Lennox et al. |
| 5,571,215 | A | 11/1996 | Sterman et al. |
| 5,573,532 | A | 11/1996 | Chang et al. |
| 5,575,766 | A | 11/1996 | Swartz et al. |
| 5,575,788 | A | 11/1996 | Baker et al. |
| 5,575,810 | A | 11/1996 | Swanson et al. |
| 5,578,007 | A | 11/1996 | Imran |
| 5,582,609 | A | 12/1996 | Swanson et al. |
| 5,588,432 | A | 12/1996 | Crowley |
| 5,590,657 | A | 1/1997 | Cain et al. |
| 5,595,183 | A | 1/1997 | Swanson et al. |
| 5,607,462 | A | 3/1997 | Imran |
| 5,617,854 | A | 4/1997 | Munsif |
| 5,630,837 | A | 5/1997 | Crowley |
| 5,637,090 | A | 6/1997 | McGee et al. |
| 5,643,197 | A | 7/1997 | Brucker et al. |
| 5,656,029 | A | 8/1997 | Imran et al. |
| 5,658,278 | A | 8/1997 | Imran et al. |
| 5,671,747 | A | 9/1997 | Connor |
| 5,673,695 | A | 10/1997 | McGee et al. |
| 5,676,662 | A | 10/1997 | Fleischhacker et al. |
| 5,676,692 | A | 10/1997 | Sanghvi et al. |
| 5,676,693 | A | 10/1997 | Lafontaine |
| 5,678,550 | A | 10/1997 | Bassen et al. |
| 5,680,860 | A | 10/1997 | Imran |
| 5,681,278 | A | 10/1997 | Igo et al. |
| 5,681,308 | A | 10/1997 | Edwards et al. |
| 5,687,723 | A | 11/1997 | Avitall |
| 5,687,737 | A | 11/1997 | Branham et al. |
| 5,688,267 | A | 11/1997 | Panescu et al. |
| 5,690,611 | A | 11/1997 | Swartz et al. |
| 5,697,536 | A | 12/1997 | Eggers et al. |
| 5,697,882 | A | 12/1997 | Eggers et al. |
| 5,697,925 | A | 12/1997 | Taylor |
| 5,697,927 | A | 12/1997 | Imran et al. |
| 5,697,928 | A | 12/1997 | Walcott et al. |
| 5,713,942 | A | 2/1998 | Stern |
| 5,716,389 | A | 2/1998 | Walinsky et al. |
| 5,718,241 | A | 2/1998 | Ben-Haim et al. |
| 5,718,701 | A | 2/1998 | Shai et al. |
| 5,720,775 | A | 2/1998 | Larnard |
| 5,722,402 | A | 3/1998 | Swanson et al. |
| 5,730,074 | A | 3/1998 | Peter |
| 5,730,127 | A | 3/1998 | Avitall |
| 5,730,704 | A | 3/1998 | Avitall |
| 5,733,280 | A | 3/1998 | Avitall |
| 5,733,281 | A * | 3/1998 | Nardella ............ 606/38 |
| 5,735,280 | A | 4/1998 | Sherman et al. |
| 5,735,290 | A | 4/1998 | Sterman et al. |
| 5,755,760 | A | 5/1998 | Maguire et al. |

| | | | |
|---|---|---|---|
| 5,769,846 A | 6/1998 | Edwards et al. | |
| 5,782,828 A | 7/1998 | Chen et al. | |
| 5,785,706 A | 7/1998 | Bednarek | |
| 5,788,636 A | 8/1998 | Curley | |
| 5,792,140 A | 8/1998 | Tu et al. | |
| 5,797,960 A | 8/1998 | Stevens et al. | |
| 5,800,428 A | 9/1998 | Nelson et al. | |
| 5,800,482 A | 9/1998 | Pomeranz et al. | |
| 5,810,802 A | 9/1998 | Panescu et al. | |
| 5,827,216 A | 10/1998 | Igo et al. | |
| 5,836,311 A | 11/1998 | Borst et al. | 128/897 |
| 5,836,947 A | 11/1998 | Fleischman et al. | |
| 5,840,030 A | 11/1998 | Ferek-Petric et al. | |
| 5,844,349 A | 12/1998 | Oakley et al. | |
| 5,846,187 A | 12/1998 | Wells et al. | |
| 5,846,191 A | 12/1998 | Wells et al. | |
| 5,849,028 A | 12/1998 | Chen | |
| 5,864,066 A | 1/1999 | Kim | 73/658 |
| 5,871,523 A | 2/1999 | Fleischman et al. | |
| 5,871,525 A | 2/1999 | Edwards et al. | |
| 5,873,845 A | 2/1999 | Cline et al. | |
| 5,876,399 A | 3/1999 | Chia et al. | |
| 5,879,295 A | 3/1999 | Li et al. | |
| 5,879,296 A | 3/1999 | Ockuly et al. | |
| 5,881,732 A | 3/1999 | Sung et al. | |
| 5,882,346 A | 3/1999 | Pomeranz et al. | |
| 5,885,278 A | 3/1999 | Fleischman | |
| 5,893,848 A | 4/1999 | Negus et al. | 606/41 |
| 5,895,417 A | 4/1999 | Pomeranz et al. | |
| 5,897,553 A | 4/1999 | Mulier et al. | |
| 5,897,554 A | 4/1999 | Chia et al. | |
| 5,899,898 A | 5/1999 | Arless et al. | |
| 5,899,899 A | 5/1999 | Arless et al. | |
| 5,902,289 A | 5/1999 | Swartz et al. | |
| 5,904,711 A | 5/1999 | Flom et al. | |
| 5,906,580 A | 5/1999 | Kline-Schoder et al. | |
| 5,906,587 A | 5/1999 | Zimmon | |
| 5,906,606 A | 5/1999 | Chee et al. | |
| 5,908,029 A | 6/1999 | Knudson et al. | |
| 5,911,694 A | 6/1999 | Ikeda et al. | 600/587 |
| 5,913,854 A | 6/1999 | Maguire et al. | 606/41 |
| 5,916,213 A | 6/1999 | Haissaguerre et al. | |
| 5,916,214 A | 6/1999 | Cosio et al. | |
| 5,919,188 A | 7/1999 | Shearon et al. | 606/41 |
| 5,921,924 A | 7/1999 | Avitall | |
| 5,921,982 A | 7/1999 | Lesh et al. | |
| 5,927,284 A | 7/1999 | Borst et al. | |
| 5,928,191 A | 7/1999 | Houser et al. | |
| 5,931,810 A | 8/1999 | Grabek | |
| 5,931,848 A | 8/1999 | Saadat | |
| 5,954,661 A | 9/1999 | Greenspon et al. | |
| 5,971,980 A | 10/1999 | Sherman | |
| 5,971,983 A | 10/1999 | Lesh | |
| 5,993,443 A | 11/1999 | Murphy-Chutorian et al. | 606/12 |
| 5,993,447 A | 11/1999 | Blewett et al. | |
| 6,004,269 A | 12/1999 | Crowley et al. | 600/439 |
| 6,007,499 A | 12/1999 | Martin et al. | |
| 6,012,457 A | 1/2000 | Lesh | |
| 6,015,404 A * | 1/2000 | Altshuler et al. | 606/9 |
| 6,016,811 A | 1/2000 | Knopp et al. | |
| 6,042,556 A | 3/2000 | Beach et al. | |
| 6,063,081 A | 5/2000 | Mulier | |
| 6,071,279 A | 6/2000 | Whayne et al. | |
| 6,088,894 A | 7/2000 | Oakley | |
| 6,096,037 A | 8/2000 | Mulier | |
| 6,113,592 A | 9/2000 | Taylor | |
| 6,117,101 A | 9/2000 | Diederich et al. | |
| 6,120,496 A | 9/2000 | Whayne et al. | |
| 6,142,993 A | 11/2000 | Whayne et al. | |
| 6,142,994 A | 11/2000 | Swanson et al. | |
| 6,152,920 A | 11/2000 | Thompson et al. | |
| 6,161,543 A | 12/2000 | Cox et al. | |
| 6,165,174 A | 12/2000 | Jacobs et al. | |
| 6,197,023 B1 | 3/2001 | Muntermann | 606/41 |
| 6,217,528 B1 | 4/2001 | Koblish et al. | |
| 6,217,576 B1 | 4/2001 | Tu et al. | |
| 6,224,592 B1 | 5/2001 | Eggers et al. | |
| 6,231,518 B1 | 5/2001 | Grabek et al. | |
| 6,235,024 B1 | 5/2001 | Tu | |
| 6,237,605 B1 | 5/2001 | Vaska et al. | |
| 6,238,347 B1 | 5/2001 | Nix et al. | |
| 6,238,393 B1 | 5/2001 | Mulier et al. | |
| 6,245,061 B1 | 6/2001 | Panescu et al. | |
| 6,245,064 B1 | 6/2001 | Lesh et al. | |
| 6,245,065 B1 | 6/2001 | Panescu et al. | |
| 6,246,898 B1 * | 6/2001 | Vesely et al. | 600/424 |
| 6,246,901 B1 | 6/2001 | Benaron | 600/431 |
| 6,251,092 B1 | 6/2001 | Qin et al. | |
| 6,251,128 B1 | 6/2001 | Knopp et al. | |
| 6,270,471 B1 | 8/2001 | Hechel et al. | |
| 6,293,943 B1 | 9/2001 | Panescu et al. | |
| 6,296,619 B1 | 10/2001 | Brisken et al. | |
| 6,302,880 B1 | 10/2001 | Schaer | |
| 6,311,692 B1 | 11/2001 | Vaska et al. | |
| 6,312,383 B1 | 11/2001 | Lizzi et al. | |
| 6,314,962 B1 | 11/2001 | Vaska et al. | |
| 6,314,963 B1 | 11/2001 | Vaska et al. | |
| 6,325,797 B1 | 12/2001 | Stewart et al. | |
| 6,328,736 B1 | 12/2001 | Mulier | |
| 6,332,881 B1 | 12/2001 | Carner et al. | |
| 6,358,248 B1 | 3/2002 | Mulier | |
| 6,361,531 B1 | 3/2002 | Hissong | |
| 6,364,876 B1 | 4/2002 | Erb et al. | |
| 6,368,275 B1 | 4/2002 | Sliwa et al. | |
| 6,371,955 B1 | 4/2002 | Fuimaono et al. | |
| 6,383,151 B1 | 5/2002 | Diederich et al. | |
| 6,385,472 B1 | 5/2002 | Hall et al. | |
| 6,391,024 B1 | 5/2002 | Sun et al. | 606/34 |
| 6,398,792 B1 | 6/2002 | O'Connor | |
| 6,409,722 B1 | 6/2002 | Hoey | |
| 6,413,254 B1 | 7/2002 | Hissong et al. | |
| 6,419,648 B1 | 7/2002 | Vitek et al. | |
| 6,425,867 B1 | 7/2002 | Vaezy et al. | |
| 6,430,426 B2 | 8/2002 | Avitall | |
| 6,440,130 B1 | 8/2002 | Mulier | |
| 6,443,952 B1 | 9/2002 | Mulier | |
| 6,447,507 B1 | 9/2002 | Bednarek et al. | |
| 6,461,314 B1 | 10/2002 | Pant et al. | |
| 6,461,956 B1 | 10/2002 | Patterson | |
| 6,464,700 B1 | 10/2002 | Koblish et al. | |
| 6,471,697 B1 | 10/2002 | Lesh | |
| 6,471,698 B1 | 10/2002 | Edwards et al. | |
| 6,474,340 B1 | 11/2002 | Vaska et al. | |
| 6,475,216 B2 | 11/2002 | Mulier | |
| 6,477,396 B1 | 11/2002 | Mest et al. | |
| 6,484,727 B1 | 11/2002 | Vaska et al. | |
| 6,488,680 B1 | 12/2002 | Francischelli | |
| 6,502,575 B1 | 1/2003 | Jacobs et al. | |
| 6,514,250 B1 | 2/2003 | Jahns | |
| 6,527,767 B2 | 3/2003 | Wang et al. | |
| 6,537,248 B2 | 3/2003 | Mulier | |
| 6,537,272 B2 | 3/2003 | Hoey | |
| 6,558,382 B2 * | 5/2003 | Jahns et al. | 606/41 |
| 5,697,536 C1 | 6/2003 | Eggers et al. | |
| 6,584,360 B2 | 6/2003 | Francischelli | |
| 6,585,732 B2 | 7/2003 | Mulier | |
| 6,605,084 B2 | 8/2003 | Acker et al. | |
| 6,610,055 B1 | 8/2003 | Swanson et al. | |
| 6,610,060 B2 | 8/2003 | Mulier | |
| 6,613,048 B2 | 9/2003 | Mulier | |
| 6,645,199 B1 | 11/2003 | Jenkins et al. | |
| 6,648,883 B2 | 11/2003 | Francischelli | |
| 6,656,175 B2 | 12/2003 | Francischelli | |
| 6,663,627 B2 | 12/2003 | Francischelli | |
| 6,692,450 B1 | 2/2004 | Coleman | |
| 6,692,490 B1 * | 2/2004 | Edwards | 606/41 |
| 6,699,240 B2 | 3/2004 | Francischelli | |
| 6,702,811 B2 | 3/2004 | Stewart et al. | |
| 6,706,038 B2 | 3/2004 | Francischelli | |
| 6,706,039 B2 | 3/2004 | Mulier | |
| 6,716,211 B2 | 4/2004 | Mulier | |
| 6,736,810 B2 | 5/2004 | Hoey | |
| 6,755,827 B2 | 6/2004 | Mulier | |
| 6,764,487 B2 | 7/2004 | Mulier | |
| 6,773,433 B2 | 8/2004 | Stewart et al. | |
| 6,776,780 B2 | 8/2004 | Mulier | |
| 6,807,968 B2 | 10/2004 | Francischelli | |

| | | |
|---|---|---|
| 6,827,715 B2 | 12/2004 | Francischelli |
| 6,849,073 B2 | 2/2005 | Hoey |
| 6,858,028 B2 | 2/2005 | Mulier |
| 6,887,238 B2 * | 5/2005 | Jahns et al. ............... 606/41 |
| 6,899,711 B2 | 5/2005 | Stewart et al. |
| 6,911,019 B2 | 6/2005 | Mulier |
| 6,916,318 B2 | 7/2005 | Francischelli |
| 6,936,046 B2 | 8/2005 | Hissong |
| 6,949,097 B2 | 9/2005 | Stewart et al. |
| 6,949,098 B2 | 9/2005 | Mulier |
| 6,960,205 B2 | 11/2005 | Jahns |
| 6,962,589 B2 | 11/2005 | Mulier |
| 2003/0045872 A1 | 3/2003 | Jacobs |
| 2003/0144656 A1 | 7/2003 | Ocel |
| 2003/0191462 A1 | 10/2003 | Jacobs |
| 2003/0216724 A1 | 11/2003 | Jahns |
| 2004/0015106 A1 | 1/2004 | Coleman |
| 2004/0015219 A1 | 1/2004 | Francischelli |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0143729 A1 | 6/2005 | Francischelli |
| 2005/0165392 A1 | 7/2005 | Francischelli |
| 2005/0209564 A1 | 9/2005 | Bonner |
| 2005/0267454 A1 | 12/2005 | Hissong |
| 2006/0009756 A1 | 1/2006 | Francischelli |
| 2006/0009759 A1 | 1/2006 | Chrisitian |

FOREIGN PATENT DOCUMENTS

| | | |
|---|---|---|
| WO | WO 01/80757 | 11/2001 |

OTHER PUBLICATIONS

Gallagher et al., "Cryosurgical Ablation of Accessory Atrioventrical Connections: A Method for Correction of the Pre-excitation Syndrome," Circulation 55(3): 471-479, 1977.
Sealy, "Direct Surgical Treatment of Arrhythmias: The Last Frontier in Surgical Cardiology," Chest 75(5): 536-537, 1979.
Sealy, "The Evolution of the Surgical Methods for Interruption of Right Free Wall Kent Bundles," The Annals of Thoracic Surgery 36(1): 29-36, 1983.
Guiraudon et al., "Surgical Repair of Wolff-Parkinson-White Syndrome: A New Closed-Heart Techique," The Annals of Thoracic Surgery 37(1): 67-71, 1984.
Klein et al., "Surgical Correction of the Wolff-Parkinson-White Syndrome in the Closed Heart Using Cryosurgery: A Simplified Approach," JACC 3(2): 405-409, 1984.
Randall et al., "Local Epicardial Chemical Ablation of Vagal Input to Sino-Atrial and Atrioventricular Regions of the Canine Heart," Journal of the Autonomic Nervous System 11:145-159, 1984.
Guiraudon et al., "Surgical Ablation of Posterior Septal Accessory Pathways in the Wolf-Parkinson White Syndrome by a Closed Heart Technique," Journal Thoracic Cardiovascular Surgery 92:406-413, 1986.
Gallagher et al., "Surgical Treatment of Arrhythmias," The American Journal of Cardiology 61:27A-44A, 1988.
Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.
Cox et al., Surgery for Atrial Fibrillation; Seminars in Thoracic and Cardiovascular Surgery, vol. 1, No. 1 (Jul. 1989) pp. 67-73.
Bredikis and Bredikis; Surgery of Tachyarrhythmia: Intracardiac Closed Heart Cryoablation; PACE, vol. 13, pp. 1980-1984.

McCarthy et al., "Combined Treatment of Mitral Regurgitation and Atrial Fibrillation with Valvuloplasty and the Maze Procedure," The American Journal of Cardiology 71: 483-486, 1993.
Yamauchi et al. "Use of Intraoperative Mapping to Optimize Surgical Ablation of Atrial Flutter," The Annals of Thoracic Surgery 56: 337-342, 1993.
Graffigna et al., "Surgical Treatment of Wolff-Parkinson-White Syndrome: Epicardial Approach Without the Use of Cardiopulmonary Bypass," Journal of Cardiac Surgery 8: 108-116, 1993.
Siefert et al., "Radiofrequency Maze Ablation for Atrial Fibrillation," Circulation 90(4): I-594.
Surgical treatment of atrial fibrillation: a review; Europace (2004) 5, S20-S29.
Elvan et al., "Radiofrequency Catheter Ablation of the Atria Reduces Inducibility and Duration of Atrial Fibrillation in Dog," Circulation 91: 2235-2244, 1995.
Cox et al., "Modification of the Maze Procedure for Atrial Flutter and Atrial Fibrillation. I. Rational and Surgical Results," The Journal of Thoracic Cardiovascular Surgery 110: 473-484, 1995.
Cox, "The Maze III Procedure for Treatment of Atrial Fibrillation," Sabiston DC, ed Atlas of Cardiothoracic Surgery, Philadelphia: WB Sauders: 460-475, 1994.
Sueda et al., "Simple Left Atrial Procedure for Chronic Atrial Fibrillation Associated with Mitral Valve Disease," The Annals of Thoracic Surgery 62(6): 1796-1800, 1996.
Tsui et al., "Maze 3 for Atrial Fibrillation: Two Cuts Too Few?" PACE 17: 2163-2166, 1994.
Kosakai et al., "Cox Maze Procedure for Chronic Atrial Fibrillation Associated with Mitral Valve Disease," The Journal of Thoracic Cardiovascular Surgery 108: 1049-1055, 1994.
Cox et al., "The Surgical Treatment of Atrial Fibrillation, IV Surgical Technique," *J of Thorac Cardiovasc Surg*, 1991: 101: 584-593.
Nardella, "Radio Frequency Energy Impedance Feedback," SPIE vol. 1068, Catheter Based Sensing and Imaging Technology (1989).
Avitall et. al., "A Thoracoscopic Approach to Ablate Atrial Fibrillation Via Linear Radiofrequency Lesion Generation on the Epicardium of Both Atria," PACE, Apr. 1996;19(Part II):626,#241.
Sie et al., "Radiofrequency Ablation of Atrial Fibrillation in Patients Undergoing Mitral Valve Surgery. First Experience," Circulation (Nov. 1996) 96:450,I-675,#3946.
Sie et al., "Radiofrequency Ablation of Atrial Fibrillation in Patients Undergoing Valve Surgery," Circulation (Nov. 1997) 84:I450,#2519.
Jais et al., "Catheter Ablation for Paroxysmal Atrial Fibrillation: High Success Rates with Ablation in the Left Atrium," Circulation (Nov. 1996) 94:I-675,#3946.
Cox, "Evolving Applications of the Maze Procedure for Atrial Fibrillation," Ann Thorac Surg, 1993;55:578-580.
Cox et al. "Five-Year Experience with the Maze Procedure for Atrial Fibrillation," Ann Thorac Surg, 1993; 56:814-824.
Avitall et al., "New Monitoring Criteria for Transmural Ablation of Atrial Tissues," Circulation, 1996;94(Supp 1):I-493, #2889.
Cox et al., "An 8 1/2 Year Clinical Experience with Surgery for Atrial Fibrillation," Annals of Surgery, 1996;224(3):267-275.
Haissaguerre et al., "Radiofrequency Catheter Ablation for Paroxysmal Atria Fibrillation in Humans: Elaboration of a procedure based on electrophysiological data," Nonpharmacological Management of Atrial Fibrillation, 1997 pp. 257-279.
Haissaguerre et al., "Right and Left Atrial Radiofrequency Catheter Therapy of Paroxysmal Atrial Fibrillation," Journal of Cardiovascular Electrophysiology, 1996;7(12):1132-1144.
Haissaguerre et al., "Role of Catheter Ablation for Atrial Fibrillation," Current Opinion in Cardiology, 1997;12:18-23.
Kawaguchi et al., "Risks and Benefits of Combined Maze Procedure for Atrial Fibrillation Associated with Organic Heart Disease," JACC, 1996;28(4):985-990.
Cox, et al., "Perinodal cryosurgery for atrioventricular node reentry tachycardia in 23 patients," Journal of Thoracic and Cardiovascular Surgery, 99:3, Mar. 1990, pp. 440-450.
Cox, "Anatomic-Electrophysiologic Basis for the Surgical Treatment of Refractory Ischemic Ventricular Tachycardia," Annals of Surgery, Aug. 1983; 198:2;119-129.
Williams, et al., "Left atrial isolation," J Thorac Cardiovasc Surg; 1980; 80: 373-380.

Scheinman, "Catheter-based Techniques for Cure of Cardiac Arrhythmias," Advances in Cardiovascular Medicine, 1996, ISSN 1075-5527, pp. 93-100.

An article entitled "Radiofrequency Ablation of Cardiac Arrhythmias" (Lawrence S. Klein and William M. Miles, Scientific American Science & Medicine May/Jun. 1994, pp. 48-57.

Comparison of cryogen spray and surface contact cooling through heat transfer modeling / E. Victor Ross, Jr., MD & Dilip Paithankar, PHD / www.lasernews.net 2000.

An article entitled "Transcatheter Radiofrequency Ablation of Atrial Tissue Using A Suction Catheter" (Th Lavergne, L. Pruner, L. Cuize, P. Bruneval, D. Von Euw, J-Y Le Heuzey and P Peronneau, (From the Inserm U 256 * 28 (*) Paris, France, PACE vol. 12 Jan. 1989 Part II pp. 177-186.

An article entitled "Radiofrequency Ablation of Atrial Fibrillation in Patients undergoing concomitant Cardiac Surgery. First Experience" (Willem P. Beukema, MD, Hauw T. Sie, MD, Anand R Ramdat Misier, MD, Max MP Haalebos, MD, Cor W. Schipper, Hospital De Weezenlanden, Zwolle, The Netherlands; PACE Apr. 1997; 20 Part II, p. 1100 (abstract only).

An article entitled "Efficacy of a Simple Left Atrial Procedure for Chronic Atrial Fibrillation in Mitral Valve Operations" (Taijiro Sueda, MD, al., Hideyuki Nagata, MD, Kazumasa Orihashi, MD, Satoru Moria, MD, Kenji Okada, MD, Masafumi Sueshiro, MD, Shinji Hirai, MD, and Yuichiro Matsuura, MD, First Department of Surgery, Hiroshima University, School of Medicine, Hiroshima Japan, 1997 by the Society of Thoracic Surgeons, pp. 1070-1075; Ann Thoracic Surg 1997:63:1075.

An article entitled "Minimally Invasive Endocardial and Epicardial Maze Procedure" (The Pennsylvania State University, Milton S. Hershey Medical Center, Hershey, Pennsylvania, Revised: Nov. 25, 1998, pp. 1-26.

Abstracts from the 70th Scientific Sessions entitled "Video-Assisted Thoraoscopic Radio Frequency Catheter Ablation of the Left Atrium Prevents Inducibility of Atrial Fibrillation in Dogs" (Philippe Chevalier, Jean-Francosi Obadia, Gilbert Kirkorian, Hopital Cardiologique, Lyon France: Quadiri Timour, Universite Lyon I, Lyon France; Bernard Bui-Xuan, Hopital Edouard Herriot, Lyon France; Paul Touboul, Hopital Cardiologique, Lyon France; Circulation 1997: 96 (8 Suppl): p. 1-575)(Abstract only).

An article from the Clinical Cardiology: Ablation Therapy—Atrial Fibrillation and Other SVT's: Tuesday Afternoon Convention Center Room 311A-D Abstracts 2517-2526 entitled "Intraoperative Observations and Epicardial Mapping after Attempted Catheter Ablation of Atrial Fibrillation," (Bruce D. Lindsay, John P. boineau, Richard B. Schuessler, Demetrios G. Lappas, James L. Cox, Washington University, St. Louis MO (Circulation 1997, 96 (8 Suppl): 450 (Abstract only).

NASPE® North American Society of Pacing and Electrophysiology 19th Annual Scientific Sessions Abstract Form entitled Can Linear, Radiofrequency Ablation Lesions Replace Surgical Incisions During Open-Heart, Atrial Maze Procedures? (James A. Caccitolo, MD, Donald N. Jensen, DVM, MS, Hartzell V. Schaff, MD, Rahul Mehra, PhD, Mayo Clinic, Rochester, MN and Medtronic, Inc., Minneapolis, MN (Abstracts, Dec. 3, 1997, Young Investigators Awards, Dec. 12, 1997 (Abstract only).

An article entitled "New Insights into the Mechanism of Chronic Atrial Fibrillation Combined With Isolated Mitral Disease and Possibility of Simple Surgical Ablation: Characteristics of Atrial Epicardium Activation Mapping During Atrial Fibrillation" (Yoko Yagi, Kohei Kawazoe, Masayuki Mukaida, Yoshitaka Shiina, Hiroshi Izumoto, Tatsuya Sasaki, Kimitaka Tasai, Takayuki Nakajima, Naoki Chiba, Iwate Medical University, Morioka Japan (Circulation 1997:96 (8, Suppl): 451 (abstract only).

An article entitled "Radiofrequency Ablation of Atrial Fibrillation in Patients Undergoing Valve Surgery" (Hauw T. Sie, Willem P. Beukema, Anand R. Ramdat Misier, Hospital de Weezenlanden, Zwolle Netherlands: Joep LRM Smeets, Academic Hospital, Maastricht Netherlands: Clemens C. Jacobs, Hospital de Weezenlanden, Zwolle Netherlands: Hein J J Wellens, Academic Hospital, Maastricht Netherlands (Circulation 1997: 96 (8 Suppl): 450-451) (Abstract only).

An article entitled "An Endocardial Radiofrequency Ablative Technique for Cure of Atrial Fibrillation During Cardiac Surgery" (Stuart P Thomas, Graham R Nunn, Ian Nicholson, Arianwen E Rees, Westmead Hospital, Sydney Australia: Michael P J Daly, CRC for Cardiac Technology, Sydney Australia: John B Uther, David L Ross, Westmead Hospital Sydney Australia (Circulation 1997: 96 (8 Suppl): 450 (Abstract only).

Identification of Enamel and Dentine Under Tooth Laser treatment / Belikov, Novirov and Scrypnik / Proceedings of Medical Applications of Lasers III, Sep. 12-16, 1995, SPIE vol. 2623 p. 109-116.

* cited by examiner

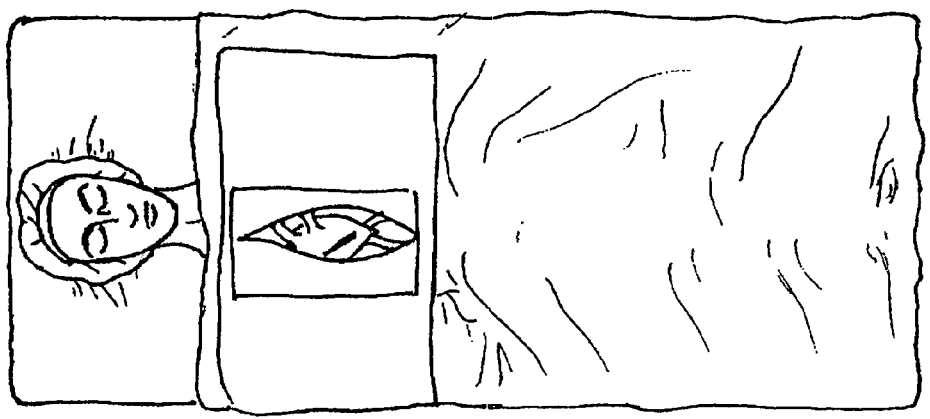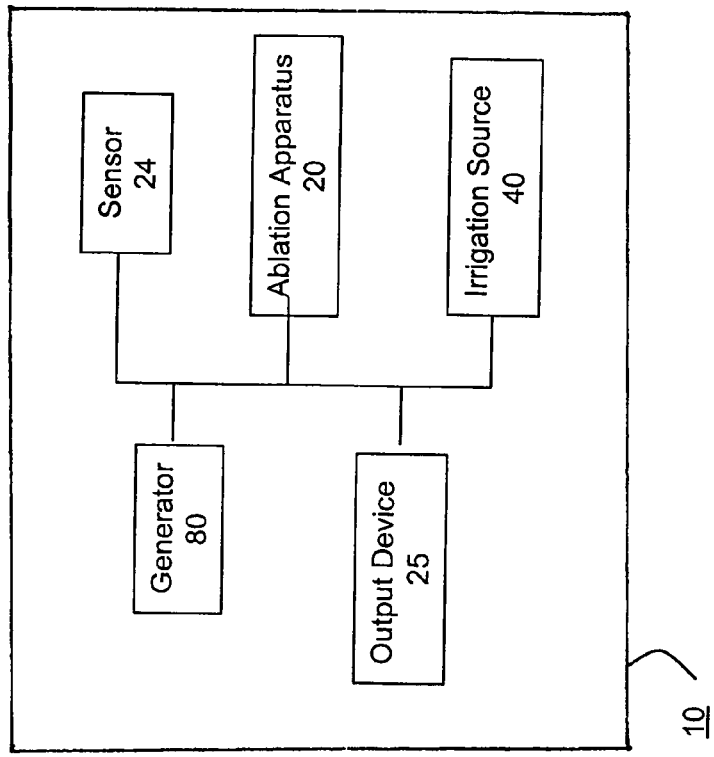
FIG. 4

VIBRATION SENSITIVE ABLATION DEVICE AND METHOD

CROSS-REFERENCE TO RELATED APPLICATION

This application is a continuation of U.S. patent application Ser. No. 09/844,221, filed Apr. 26, 2001, now abandoned, which is a continuation-in-part of U.S. patent application Ser. No. 09/559,604, filed Apr. 27, 2000, now abandoned.

FIELD OF THE INVENTION

This invention relates to ablation devices that are used to create lesions in tissue. More particularly, this invention relates to ablation devices that are capable of monitoring the level of energy being used to ablate the tissue and of preventing the energy from creating tissue-damaging events such as a "steam pop."

BACKGROUND OF THE INVENTION

The action of the heart is known to depend on electrical signals within the heart tissue. Occasionally, these electrical signals do not function properly. The maze procedure is a surgical operation for patients with atrial fibrillation that is resistant to medical treatment. In this procedure, incisions are created in the right and left atria to produce an orderly passage of the electrical impulse from the SA node to the atrioventricular node. Blind passageways are also created to suppress reentry cycles. Currently, the lesions may still be created using a traditional cut and sew technique. The scar tissue resulting from the procedure results in a non-conductive lesion.

Ablation of cardiac conduction pathways in the region of tissue where the signals are malfunctioning is now being used to replace the surgical incisions. Ablation is used with other organ tissue, such as the lung, liver, prostate and uterus. Ablation of organic tissue, such as heart, lung or liver tissue, is a technique used in several surgical procedures, for both diagnosis and therapy. In one instance, electrodes at the tips of an electrophysiology ablation device allow the physician to measure electrical signals along the surface of the heart (mapping). In another instance, the physician may also ablate certain tissues using energy (such as radiofrequency energy) conducted to one or more ablation electrodes. Higher levels of energy are used to cut and remove tissue (electrosurgery). Lower levels of energy are used to cause cell damage but leave the structure intact so that electrical pathways are blocked within the tissue.

Sometimes ablation is necessary only at discrete positions along the tissue. This is the case, for example, when ablating accessory pathways, such as in Wolff-Parkinson-White syndrome or AV nodal reentrant tachycardias. At other times, however, ablation is desired along a line, called linear ablation. This is the case for atrial fibrillation, where the aim is to reduce the total mass of contiguous (electrically connected) atrial tissue below a threshold believed to be critical for sustaining multiple reentrant wavelets. Linear lesions are created between electrically non-conductive anatomic landmarks to reduce the contiguous atrial mass.

Linear ablation is currently accomplished in one of several ways. One way is to position the tip portion of the ablation device so that an ablation electrode is located at one end of the target site. This may be done, for example, with an electrode positioned on a "pen-like" device. Then energy is applied to the electrode to ablate the tissue adjacent to the electrode. The tip portion of the electrode is then slid along the tissue to a new position and then the ablation process is repeated. This is sometimes referred to as the "spot burn" technique. This technique is time-consuming (which is not good for the patient) and requires multiple accurate placements of the electrode (which may be difficult for the physician).

Another way of accomplishing linear ablation is to use an ablation device having a series of spaced-apart band or coil electrodes which, after the electrode portion of the ablation device has been properly positioned, are energized simultaneously or one at a time to create the desired lesion. If the electrodes are close enough together the lesions run together sufficiently to create a continuous linear lesion. While this technique eliminates some of the problems associated with the "spot burn" technique, some repositioning of the ablation device may be required to create an adequately long lesion. In addition, it may be difficult to obtain adequate tissue contact pressure for each electrode in a multi-electrode ablation device.

A variety of devices may be used to ablate tissue. Typically, such devices include a conductive tip, which serves as one electrode in an electrical circuit. The electrical circuit is completed via a grounding electrode that may also be on the device or may be coupled to the patient. By controlling the level of energy transmitted to the ablation electrode, the user is able to control the amount of heat generated for the purposes described above. The ablation site may also be irrigated to cool the electrode and create greater lesion depth.

In order to control the level of energy transmitted, the user must monitor the level of energy being transmitted from the electrode. Typical systems for monitoring ablation energy rely on temperature. A thermocouple element is located within the ablation device, generally near the electrode. This temperature-measuring element effectively measures the temperature of the electrode rather than the tissue being ablated. Particularly when the site is being irrigated with a conductive fluid, the temperature of the tissue may differ to some degree from the temperature of the ablation device.

Additionally, water (from within and around the tissue) is present at the ablation site. The heat required to raise the temperature of liquid water by 1° C. is 1.0 kcal/g. However, due to the unique chemical structure of the water molecule, additional heat is required for water to change phase from the liquid to gaseous phase. If the temperature at the ablation site exceeds 100° C., the water will change phase, boil and may result in an audible "steam pop" within the tissue. This pop may damage and even rupture the tissue. Irrigation cooling of the site shifts the location of the "steam pop" even deeper within the tissue, resulting in even greater damage than a superficial pop.

It has been observed that before a "steam pop", there is a mechanical vibration within the tissue (suspected to be caused by the phase transition of water, which may create microbubbles within the tissue). This vibration transfers to the ablation device. A sensitive enough instrument and a sensitive enough user may perceive this vibration in time to halt ablation, for example, by turning off the energy being delivered to the ablation device. However, due to such reasons as slow human reaction, vibration damping from the device or vibration damping from the tissue, the user is often not able to halt or modify ablation in time to prevent damage.

Thus a means for sensing this vibration in time to halt or modify ablation would be desirable. In addition, a means of automatically halting ablation or modifying the amount of ablation energy being transmitted when this vibration occurs would also be desirable. Moreover, a means of alerting a user to halt or modify ablation would also be desirable.

SUMMARY OF THE INVENTION

One aspect of the invention provides an ablation apparatus. The apparatus may include a maneuvering mechanism, a conductive element attached to the mechanism, a sensor attached to the mechanism and an output device attached to the sensor. The sensor may sense vibration during an ablation procedure, including the excitation of water molecules within tissue being ablated and the vibration of the conductive element. Upon sensing this vibration, the sensor may send a signal to the output device to respond to the signal by reducing or halting power to the conductive element. The apparatus may also give a visual or audio signal to a user to control the power. The sensor may also control a fluid supply in a similar manner. The sensor may be integrated with the conductive element. The sensor may be, for example, a microphone, an accelerometer, or a piezoelectric crystal. The maneuvering mechanism may be, for example, a hemostat-like handle or a catheter.

Another aspect of the invention provides for an ablation apparatus including a maneuvering mechanism. The maneuvering mechanism may include a conductive element, a sensor adjacent the conductive element and an output device in communication with the conductive element. The sensor may sense vibration caused by an ablation procedure and send a signal to the output device to reduce or turn off power to the conductive element. The output device may also signal the user to control the power to the conductive element. The sensor may be a piezoelectric crystal, a piezoelectric polymer or a mechanical sensor. The sensor may be integrated with the conductive element. The maneuvering mechanism may be, for example, a hemostat-like handle or a catheter.

Another aspect of the invention provides a method of ablating organic tissue. A conductive element may be positioned adjacent the organic tissue. Power may be supplied to the element to ablate the tissue. A sensor maybe be positioned adjacent the conductive element to sense the vibration of the organic tissue. When the vibration reaches a given value, power to the conductive element may be reduced or turned off. The sensor may also send a signal via an output device to reduce or turn off power. A related method may be used to turn off or reduce fluid being supplied to the tissue. The sensor may be a piezoelectric crystal, a piezoelectric polymer. The sensor may be integrated with the conductive element.

The foregoing and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

BRIEF DESCRIPTION OF THE DRAWINGS

FIG. 4 is illustrates an alternative embodiment of a system for ablating tissue in accordance with the present invention.

DETAILED DESCRIPTION OF THE PRESENTLY PREFERRED EMBODIMENTS

Figure 1:
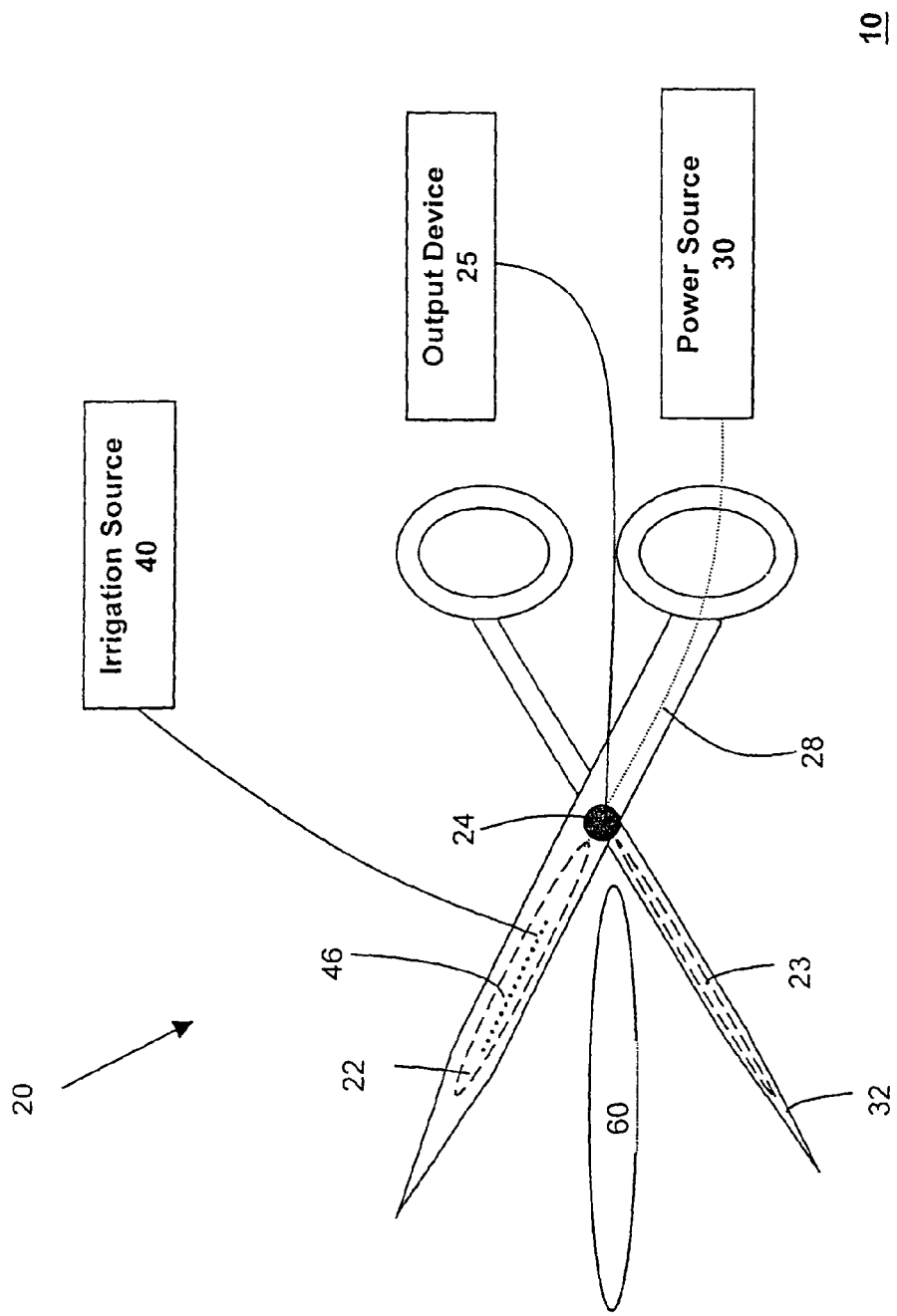
FIG. 1 is a schematic view of a system for ablating tissue in accordance with the present invention.

FIG. 1 shows a system 10 for ablating tissue in accordance with the present invention. Typically the tissue to be ablated may be located within the body cavity, such as the endocardial or epicardial tissue of the heart. Other body organ tissue, such as the liver or lung, may also be ablated using the present invention. System 10 may include an ablation apparatus 20 that comprises a conductive electrode 22, a sensor 24 connected to an output device 25 and a connection 28 to a source of ablation energy. System 10 may further include a power source 30 that provides ablation energy. System 10 may also include an indifferent (non-ablating) electrode 23 which may serve as the return plate for energy transmitted through electrode 22. Electrode 23 may be placed elsewhere on the patient's body than the ablation site. For example, electrode 23 may be placed on the patient's back or thigh. System 10 may further include an irrigation source 40 that provides irrigation fluid to the ablation site. Ablation apparatus 20 or electrode 22 of ablation apparatus 20 may also include fluid openings 46 through which irrigation fluid may flow to the site.

In use, a user may manipulate ablation apparatus 20 so that electrode 22 contacts the surface of the tissue to be ablated. Power source 30 provides energy to the apparatus 20 via connection 28. This connection may be any suitable connection for conducting energy from power source 30 to apparatus 20. Power source 30 may be any suitable power source such as, for example, standard electrical power available in the operating room. Once power source 30 is turned on, the user may use apparatus 20 to ablate the tissue with energy from source 30.

As ablation occurs, it is sometimes desirable to irrigate the ablation site with irrigation fluid, which may be, for example, any suitable fluid such as saline or another conductive fluid. The irrigating fluid may cool the electrode 22 of ablation apparatus 20 and may allow for greater lesion depth. Furthermore, continuous fluid flow may keep the ablation device surface temperature below the threshold for blood coagulation, which may clog the device. Use of irrigating fluid may therefore reduce the need to remove a clogged ablation device for cleaning or replacement. The presence of an ionic fluid layer between electrode 22 and the tissue to be ablated may also ensure that an ionic fluid layer conforming to the tissue contours is created. In one preferred embodiment, saline solution is used. Alternatively, other energy-conducting liquids, such as Ringer's solution, ionic contrast, or even blood, may be used. Diagnostic or therapeutic agents, such as lidocaine, $CA^{++}$ blockers, ionic contrast, or gene therapy agents may also be delivered before, with or after the delivery of the irrigating fluid. Irrigation source 40 may be any suitable source of irrigation fluid such as, for example, a standard irrigation pump (not shown). This pump may also be connected to power source 30 or may have its own source of power. Preferably, apparatus 20 may also include means for delivering irrigation to the ablation site from irrigation source 40. Such means may be, for example, fluid openings 46.

Figure 2:
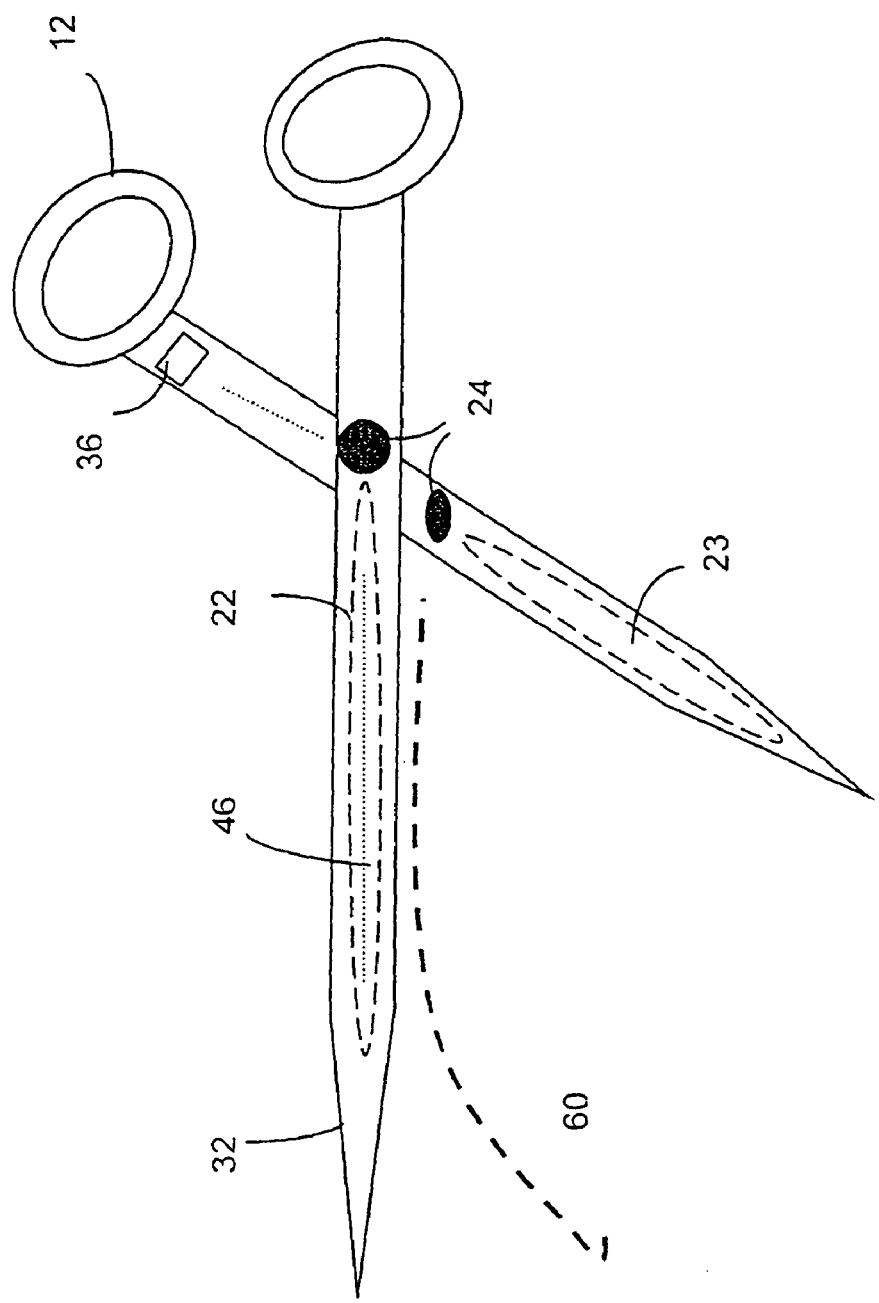
FIG. 2 is a schematic view of one embodiment of an ablation apparatus in accordance with the present invention.

FIG. 2 shows a perspective view of ablation apparatus 20. Ablation apparatus 20 may be any suitable ablation tool such as, for example, a catheter, an electrocautery device, an electrosurgical device, a suction-assisted ablation tool, an ablation pod, an ablation paddle, an ablation hemostat or an ablation wire. Ablation apparatus 20 or its components are preferably made of a biocompatible material such as stainless steel, biocompatible epoxy or biocompatible plastic. Preferably a biocompatible material prompts little allergenic response from the patient's body and is resistant to corrosion from being placed within the patient's body. Furthermore, the biocompatible material preferably does not cause any additional stress to the patient's body, for example, it does not scrape detrimentally against any elements within the surgical cavity.

Preferably, ablation apparatus 20 may be permanently or removably attached to or incorporate a maneuvering apparatus for manipulating apparatus 20 onto a tissue surface. Such an apparatus may be, for example, hemostat handles 12 as shown in FIGS. 1 and 2. Electrodes of ablation apparatus 20 may be located on one or more of the hemostat jaws 32. Alternatively conductive electrode 22 of ablation apparatus 20 may be mounted on a pen-like maneuvering apparatus. Ablation apparatus 20 may also include an appropriate catheter handle, such as, for example, the handle of a transvenous catheter. Ablation apparatus 20 may also be maneuvered with a leash or pull-wire assembly. Alternatively any appropriate flexible or rigid handle may be used as a maneuvering apparatus. Alternatively, any appropriate endoscopic or thoroscopic maneuvering apparatus may also be used with ablation apparatus 20.

Apparatus 20 also preferably includes a connection 28 suitable for conducting energy to apparatus 20, particularly to conductive element 22 from a power source.

The conductive element 22 of ablation apparatus 20 is preferably an electrode 22. This electrode 22 may be positioned in any suitable place on apparatus 20. Preferably electrode 22 is placed near an end of the apparatus 20, away from the user, to be more easily manipulated against the tissue 60 to be ablated. As shown in the embodiment of FIG. 2, apparatus 20 may incorporate an anode electrode 22 and a cathode electrode 23 in a bipolar circuit. The two electrodes 22, 23 may be arranged on the jaws of a hemostat-like tool. Electrodes 22, 23 may each be, for example, weeping electrodes, double wound coil electrodes, electrode needles or any other suitable electrode.

Figure 3:
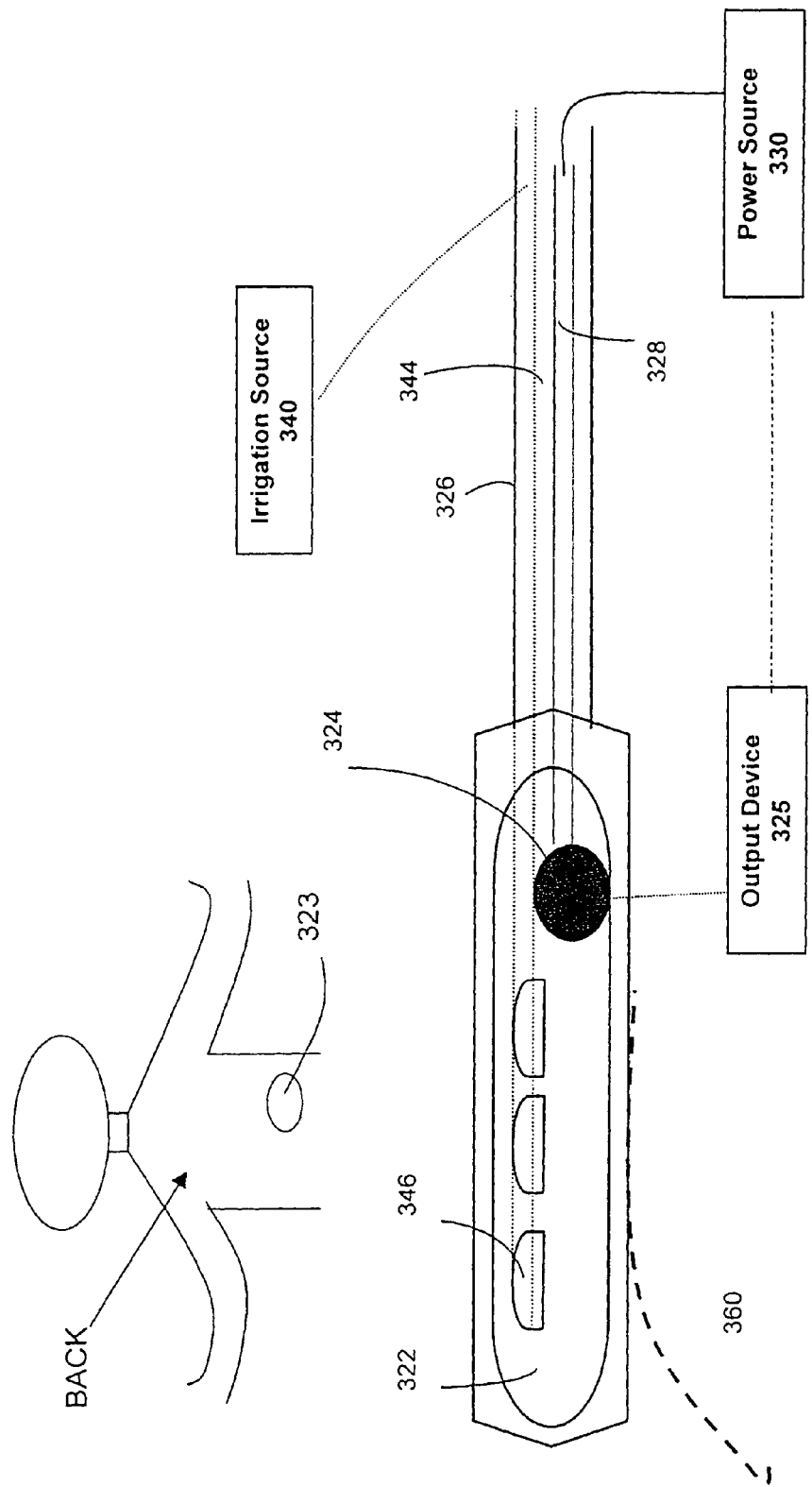
FIG. 3 is a side view of another embodiment of an ablation apparatus in accordance with the present invention.

As FIG. 2 shows, a sensor 24 may be permanently or removably incorporated into apparatus 20. This sensor 24 may sense the vibration in tissue that occurs prior to a "steam pop" as described above. Sensor 24 may sense this vibration in time to alert the user to halt ablation. Preferably, sensor 24 may sense the vibration of the tissue. Alternatively, the vibration of the tissue may be transferred to the apparatus 20 and sensor 24 may sense the vibration of the device. In the embodiment of FIG. 2, this sensor 24 may be incorporated into the apparatus 20, preferably near one of the electrodes 22, 23. The vibration signal from tissue 60 becomes more dampened the farther away from the ablation site sensor 24 is placed. Thus, sensor 24 is preferably located as close as possible to the ablation site. For example, as shown in FIG. 2, sensor 24 may be located near the tip of one or more jaws of a hemostat-like tool. Alternatively, as shown in FIG. 3, sensor 24 may be located near the tip of a catheter-type tool, such as an intravenous catheter.

Apparatus 20 may include a separate sensor for each of electrodes 22, 23, as seen in FIG. 2. Apparatus 20 may also include one sensor that may serve its function for both electrode 22 and electrode 23, as seen in FIG. 1. Apparatus 20 may also have a series of sensors along the entire length of the device, particularly if the device is longer, such as a catheter. Placement of a series of sensors on apparatus 20 may ensure that at least one sensor will be located near the ablation site no matter how long the device.

Sensor 24 is preferably a piezoelectric crystal highly sensitive to vibration. Sensor 24 may also be a piezoelectric polymer. The signal given out by such a piezoelectric crystal or polymer is proportional to the amount of vibration it senses. Thus, the intensity of the signal transmitted by sensor 24 corresponds to the intensity of the vibration. A piezoelectric element or accelerometer is typically attached to or placed near a vibrating structure (such as, for example, vibrating tissue). As the vibrating structure moves relative to its surrounding space, its mass exerts an inertial force on the piezoelectric element. The exerted force produces a proportional electric charge on the piezoelectric element.

Alternatively, sensor 24 may be, for example, a microphone. Sensor 24 may also be any suitable mechanical sensor of appropriate dimensions for incorporation into an ablation apparatus 20.

The signal from sensor 24 may preferably be amplified by a suitable amplifier (not shown) before reaching output device 25. The amplifier may be incorporated into output device 25. Alternatively the amplifier may be incorporated into ablation apparatus 20. Alternatively, the amplifier may be a separate device.

Output device 25 may receive and preferably interpret the signal from sensor 24. For example, output device 25 may be capable of filtering out signals that differ from the signal resulting from a "steam pop" vibration. For example, the signal from the vibration of someone tapping on the operating table may be differentiated from the signal resulting from a "steam pop" vibration. Such filtering of vibration signals may be programmed in software using appropriate algorithms. Alternatively, the filtering of vibration signals may be designed into hardware electronics.

Output device 25 may be a device separate from power source 30 and irrigation source 40. Output device 25 may also be incorporated into power source 30, irrigation source 40, or ablation apparatus 20.

In one embodiment, sensor 24 is a piezoelectric element and may generate a voltage as its signal. Sensor 24 may generate this voltage without any additional power. If necessary, for example, for another type of sensor, connection 28 described above may provide power to sensor 24 from power source 30. Sensor 24 may also have its own connection and/or its own power source for additional power if necessary.

In use, while the user is ablating the tissue 60, the water at the ablation site may begin to simmer and vibrate accordingly. Simmering and vibration may occur if the site is irrigated or not. Water at the site may be water from within or around the tissue. If this simmering continues unabated, a "steam pop" as described above, will occur. Such a simmering vibration may be sensed by sensor 24 which will produce a signal to output device 25. For example, output device 25 may preferably comprise a switch or regulator, which, at a signal from sensor 24, adjusts power, turns on power and/or turns off power from source 30. Such an automatic feedback system for interrupting ablation energy may prevent the "steam pop." If the ablation site is being irrigated from irrigation source 40, the switch or regulator may also adjust fluid flow, turn on fluid flow and/or turn off fluid flow from irrigation source 40.

Alternatively, output device 25 may control the power level from the power source 30. For example, a signal of a first intensity from sensor 24 may indicate that the power level from power source 30 should be lowered; a signal of a different intensity may indicate that the power source 30 should be turned off. Preferably, device 25 may be configured so that it may automatically raise or lower the power from source 30 appropriately. Alternatively, the control of power source 30 based on output from output device 25 may be manual.

Output device 25 may also be a visual display that indicates to the user that ablation energy should be halted. Such a display may be, for example, an indicator on a monitor. In one example, the monitor may display the voltage corresponding to the signal emitted from sensor 24. This signal corresponds in turn to the intensity of the vibration at the tissue site. Therefore a voltage level of 2 would indicate that the tissue was vibrating more intensely than when the voltage level was 1. In this example, a user would monitor the voltage level and, if it exceeded a certain value, would turn off or adjust the power source 30.

Alternatively, the display of device 25 may be located on the apparatus 20 itself, as shown in FIG. 2. In this embodiment, an indicator 36, such as an LED light is permanently or removably incorporated into apparatus 20. The indicator 36 may receive a signal from sensor 24 indicating that the tissue vibration had reached a level that might indicate an impending "steam pop." In response, indicator 36 may turn on, change color, grow brighter or change in any suitable manner to indicate that the flow of power from source 30 should be modified or halted. The indicator may also be located on power source 30, on irrigation source 40, or may be located on another location visible to the user.

Alternatively, output device 25 may be an audio device that indicates to the user that ablation energy should be halted. Such an audio device may be, for example, a speaker that broadcasts a sound (for example, a beep) that increases in intensity, frequency or tone as the intensity of the vibration sensed by sensor 24 increases. The user may adjust, for example, turn down or turn off power source 30 when the sound emitted reaches a given volume or level. In another embodiment, the audio device may also give an audible signal (such as the message "turn off power source") when the intensity of the vibration sensed by sensor 24 reaches a certain level. Such an audio device may be located on the ablation apparatus 20 itself, on power source 30, or on irrigation source 40. The audio device may also be a separate device.

FIG. 3 shows another embodiment of ablation apparatus 320 in which cathode electrode 323 may be placed elsewhere than on apparatus 320. In such a monopolar arrangement, for example, anode electrode 322 is positioned on the tissue 360 to be ablated. Meanwhile, cathode electrode 323 may be placed on the patient's back, thigh or elsewhere on the patient. Apparatus 320 also includes a handle 326 and a connection 328 to power source 330.

In the embodiment of FIG. 3, apparatus 320 may incorporate fluid openings 346 into the electrode 322. These fluid outlets may be connected to a conduit 344 that conducts irrigation fluid from irrigation source 340.

FIG. 3 shows that apparatus 320 may integrate sensor 324 into electrode 322. For example, electrode 322 may be located near a distal tip of an intravenous catheter and sensor 324 may be integrated into electrode 322 at the tip. This sensor 324 may act in the manner described above to sense the vibration of an impending "steam pop." Sensor 324 may then produce a signal to output device 325. Output device 325 is preferably a switch or regulator that, at the signal from sensor 324, adjusts or turns power source 330 off. Such an automatic feedback system for interrupting ablation energy may prevent the "steam pop." It is contemplated that the switch or regulator may also be able to turn irrigation source 340 off. In FIG. 3, output device 325 is shown as a separate device connected to power source 330. Output device 325 may also be located on power source 330, irrigation source 340, or may be located on ablation device 320.

Alternatively, output device 325 may produce a visual or audio signal such as those described above to indicate that ablation should be halted.

It is contemplated that the ablation device of the present invention may incorporate additional devices, such as, for example, thermocouple elements to measure the temperature of the device or suction devices to better anchor the device to the tissue. It is further contemplated that the vibration sensitive ablation device of the present invention may be used in a variety of ablation systems such as those available from Medtronic, Inc., Minneapolis, Minn.

FIG. 4 shows a schematic view of another embodiment of system 10 for ablating tissue in accordance with the present invention. In this embodiment, system 10 is shown to comprise ablation apparatus 20, an output device 25, an irrigation source 40, a generator 80, and a sensor 24. As mentioned earlier, system 10 may also include an indifferent (non-ablating) electrode 23 (not shown in FIG. 6). As shown in FIG. 1, the indifferent electrode 23 may be placed elsewhere on the patient's body such as the back, thigh or shoulder or another site other than the ablation site.

Ablation apparatus 20 may comprise one or more suction elements and a suction conduit that provides suction from a suction source. Ablation apparatus 20 may also comprise a conduit that provides irrigation fluid from irrigation source 40. In addition, ablation apparatus 20 may comprise a connector for connecting ablation apparatus 20 to generator 80.

As discussed earlier, ablation apparatus 20 and its components are preferably made of a biocompatible material. Biocompatible materials or biomaterials are usually designed and constructed to be placed in or onto tissue of a patient's body or to contact fluid of a patient's body. Ideally, a biomaterial will not induce undesirable reactions in the body such as blood clotting, tumor formation, allergic reaction, foreign body reaction (rejection) or inflammatory reaction; will have the physical properties such as strength, elasticity, permeability and flexibility required to function for the intended purpose; may be purified, fabricated and sterilized easily; will substantially maintain its physical properties and function during the time that it remains in contact with tissues or fluids of the body.

Materials that are either biocompatible or may be modified to be biocompatible and may be used to make ablation apparatus 20, sensor 24 and/or their components may include metals such as titanium, titanium alloys, TiNi alloys, shape memory alloys, super elastic alloys, aluminum oxide, platinum, platinum alloys, stainless steels, stainless steel alloys, MP35N, elgiloy, haynes 25, stellite, pyrolytic carbon, silver carbon, glassy carbon, polymers or plastics such as polyamides, polycarbonates, polyethers, polyesters, polyolefins including polyethylenes or polypropylenes, polystyrenes, polyurethanes, polyvinylchlorides, polyvinylpyrrolidones, silicone elastomers, fluoropolymers, polyacrylates, polyisoprenes, polytetrafluoroethylenes, rubber, minerals or ceramics such as hydroxapatite, epoxies, human or animal protein or tissue such as bone, skin, teeth, collagen, laminin, elastin or fibrin, organic materials such as wood, cellulose, or compressed carbon, and other materials such as glass, and the like. Materials that are not considered biocompatible may be modified to become biocompatible by a number of methods well known in the art. For example, coating a material with a biocompatible coating may enhance the biocompatibility of that material.

One or more surfaces of ablation apparatus 20, sensor 24 and/or their components may be coated with one or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand). Biological agents may be found in nature (naturally occurring) or may be chemically synthesized by a variety of methods well known in the art.

Ablation apparatus 20 may comprise a surgeon controlled switch. For example, a switch may be incorporated in or on ablation apparatus 20 or any other location easily and quickly accessed by the surgeon for regulation of ablation apparatus 20 by the surgeon. The switch may be, for example, a hand switch, a foot switch, or a voice-activated switch comprising voice-recognition technologies.

A visual and/or audible signal used to alert a surgeon to the completion or resumption of ablation may be incorporated into ablation apparatus 20. For example, a beeping tone or flashing light that increases in frequency as the ablation period ends or begins may be used.

Ablation apparatus 20 may be positioned and used, for example, through a thoracotomy, through a sternotomy, percutaneously, transvenously, arthroscopically, endoscopically, for example, through a percutaneous port, through a stab wound or puncture, through a small incision, for example, in the chest, in the groin, in the abdomen, in the neck or in the knee, or in combinations thereof. It is contemplated that ablation apparatus 20 may be used, for example, in open-chest surgery on a heart in which the sternum is split and the rib cage opened with a retractor. It is also contemplated that ablation apparatus 20 may be used, for example, in closed-chest surgery on a heart in which the sternum is not split.

Figure 5:
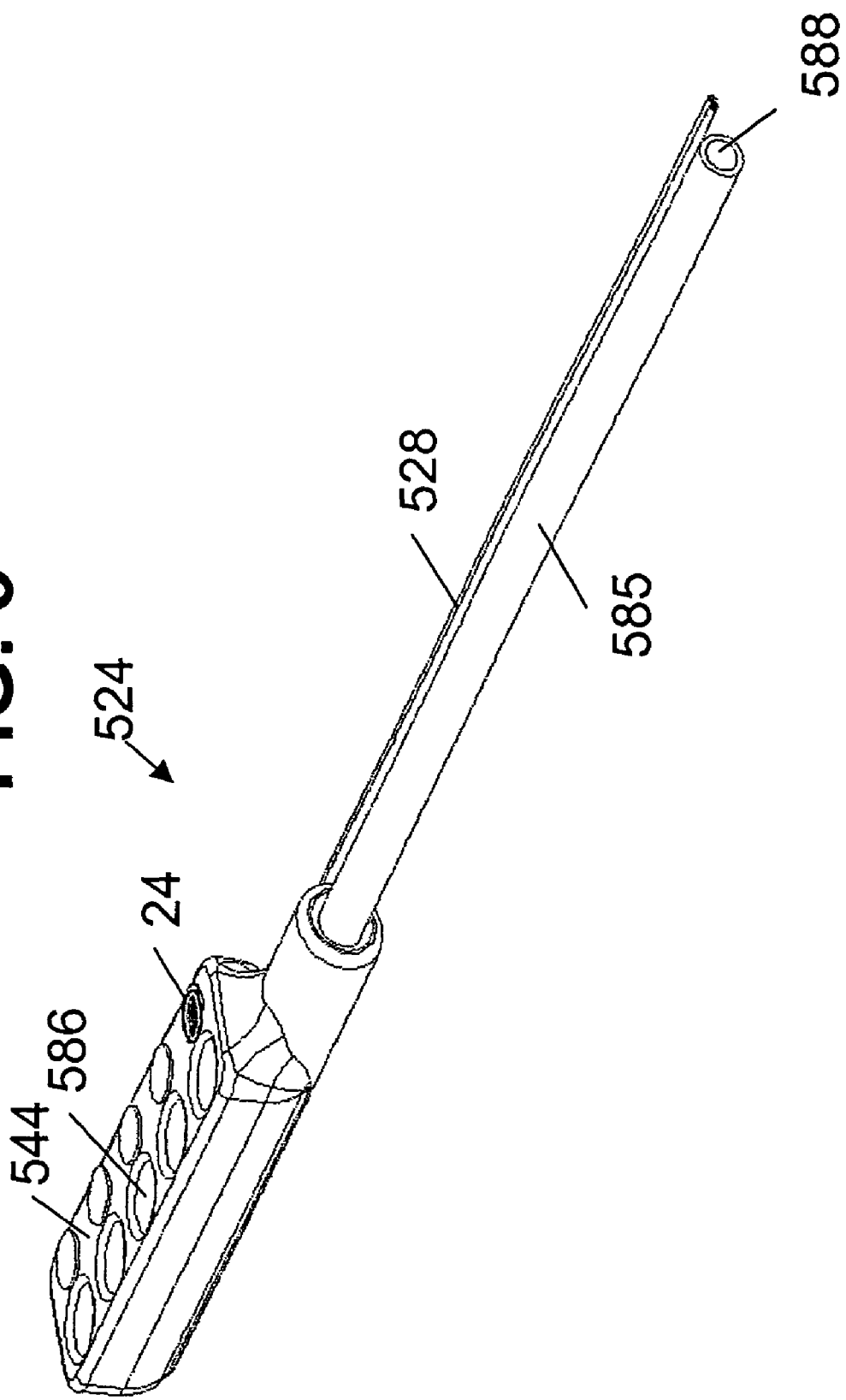
FIG. 5 illustrates an alternative embodiment of a sensor device for sensing vibration and tissue temperature in accordance with the present invention.

System 10 may also include a suction source (not shown) for providing suction to ablation apparatus 20. Ablation apparatus 20 may comprise one or more suction devices, elements or ports to better anchor ablation apparatus 20 to tissue. Suction may also be used to anchor sensor 24 to a surface of tissue. FIG. 5 shows an alternative embodiment of sensor 24 wherein sensor 24 is integrated into sensor device 524 that may be used at an alternative location to ablation apparatus 20. In this embodiment, sensor device 524 may comprise one or more suction elements, openings, orfices, or ports 586 positioned or integrated within or along a tissue contact or support surface 544. Suction openings of ablation apparatus 20 and sensor device 524 may communicate suction through a tissue contact surface to the atmosphere. Sensor device 524 may be powered by any suitable power source. For example, connection 528 may provide power to sensor 24 from power source 30, generator 80, or output device 25.

Support surface 544 may be attached to a flexible or rigid hose or tubing for supplying suction from a suitable suction source to the target tissue surface through suction ports 586 of sensor device 524. Support surface 544 may be attached to a maneuvering means for placing or positioning sensing elements against tissue. For example, sensor device 524 may comprise shaft or handle 585 coupled to support surface 544. Handle 585 may comprise suction lumen 588 for communicating suction from a suitable suction source to the target tissue surface through suction ports 586 of sensor device 524. Suction conduit or lumen 588 may be connected to least one suction port 586 containing a suction opening. Suction ports 586 may be arranged in any suitable fashion, such as a row or circle. In addition, the specific number of ports and their position may vary. Sensor device 524 may be covered with a removable covering during insertion into a patient's body to prevent blood or tissue from clogging suction openings 586, although this is not necessary. Such coverings may include coverings of biocompatible material that would cover sensor device 524. Alternatively, coverings may be placed over ports 586, such as, for example, mesh coverings or ribbed coverings.

Each suction port or opening 586 may have a suction aperture coupling port 586 with conduit 588. Suction aperture may be located in the center or at a position slightly off-center of suction port 586. Suction aperture may be any shape including circular. The suction ports 586 may also be any suitable shape, for example circular, oval, rectangular, or triangular.

Preferably, each suction aperture would have a smaller diameter than the area of suction port 586. This creates a high resistance pathway between suction port 586 and suction conduit 588. Because of this, loss of a tissue-to-port seal in one suction port (and thus loss of fixation of the suction port to the tissue) should not cause a precipitous pressure drop in the remainder of the suction ports.

Suction may be provided to ablation apparatus 20 and/or sensor device 524 by the standard suction available in the operating room. The suction source may be coupled to ablation apparatus 20 and/or sensor device 524 with a buffer flask. Suction may be provided at a negative pressure of between 200-600 mm Hg with 400 mm Hg preferred. Alternatively, suction may be provided via a manual or electric pump, a syringe, a suction or squeeze bulb or other suction or vacuum producing means, device or system. The suction source may comprise one or more vacuum regulators, valves, e.g., vacuum releasing valves, conduits, lines, tubes and/or hoses. The conduits, lines, tubes, or hoses may be flexible or rigid. For example, a flexible suction line may be used to communicate suction to ablation apparatus 20 and/or sensor device 524, thereby allowing ablation apparatus 20 and/or sensor device 524 to be easily manipulated by a surgeon. Another method that would allow the surgeon to easily manipulate ablation apparatus 20 and/or sensor device 524 includes incorporation of a suction source into ablation apparatus 20 and/or sensor device 524. For example, a small battery operated vacuum pump may be incorporated into ablation apparatus 20 and/or sensor device 524.

The suction source may be slaved to ablation apparatus 20, output device 25, irrigation source 40, generator 80 and/or sensor 24. For example, the suction source may be designed to automatically stop suction when ablation is stopped and to start suction when ablation is began. The suction source may include a visual and/or audible signal used to alert a surgeon to any change in suction. For example, a beeping tone or flashing light may be used to alert the surgeon when suction is present.

Figure 6:
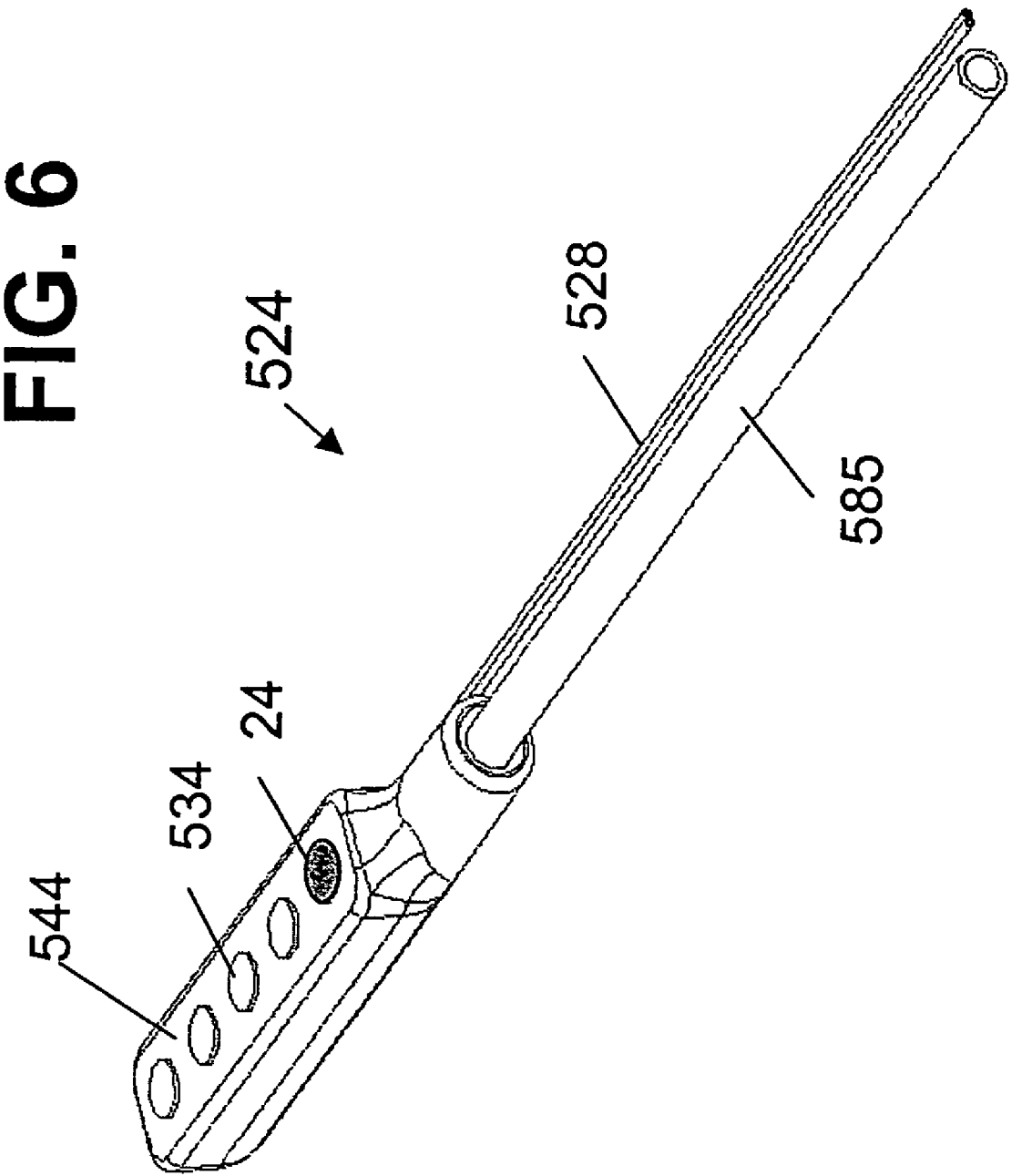
FIG. 6 illustrates an alternative embodiment of a sensor device for sensing vibration and tissue temperature in accordance with the present invention.

FIG. 6 shows an alternative embodiment of sensor device 524 comprising sensor 24 and a plurality of temperature-sensing elements 534 aligned in a row on a support surface 544. Support surface 544 may be attached to shaft or handle 585. Handle 585 may be rigid or flexible. Handle 585 may comprise one or more hinges or joints (not shown) for maneuvering and placing sensor 24 against tissue. The hinges or joints of handle 585 may be actuated remotely, for example, from outside a patient's body. Handle 585 may be malleable or shapeable. Connection 528 may provide power to sensor device 524 from power source 30, generator 80, or output device 25.

Sensor device 524 may be positioned and used, for example, through a thoracotomy, through a sternotomy, percutaneously, transvenously, arthroscopically, endoscopically, for example, through a percutaneous port, through a stab wound or puncture, through a small incision, for example, in the chest, in the groin, in the abdomen, in the neck or in the knee, or in combinations thereof. It is contemplated that sensor device 524 may be used, for example, in open-chest surgery on a heart in which the sternum is split and the rib cage opened with a retractor. It is also contemplated that sensor device 524 may be used, for example, in closed-chest surgery on a heart in which the sternum is not split.

Sensor device 524 may include or be operatively coupled with a surgeon-controlled switch. For example, a switch may be incorporated in or on sensor device 524 or any other location easily and quickly accessed by the surgeon for regulation of sensor 24 by the surgeon. The switch may be, for example, a hand switch, a foot switch, or a voice-activated switch comprising voice-recognition technologies.

Sensor device 524 may include, or may be coupled with a device that generates, a visual and/or audible signal used to alert a surgeon to any change in tissue temperature. For example, a beeping tone or flashing light may be used to alert the surgeon that a change has occurred in tissue temperature.

Figure 7:
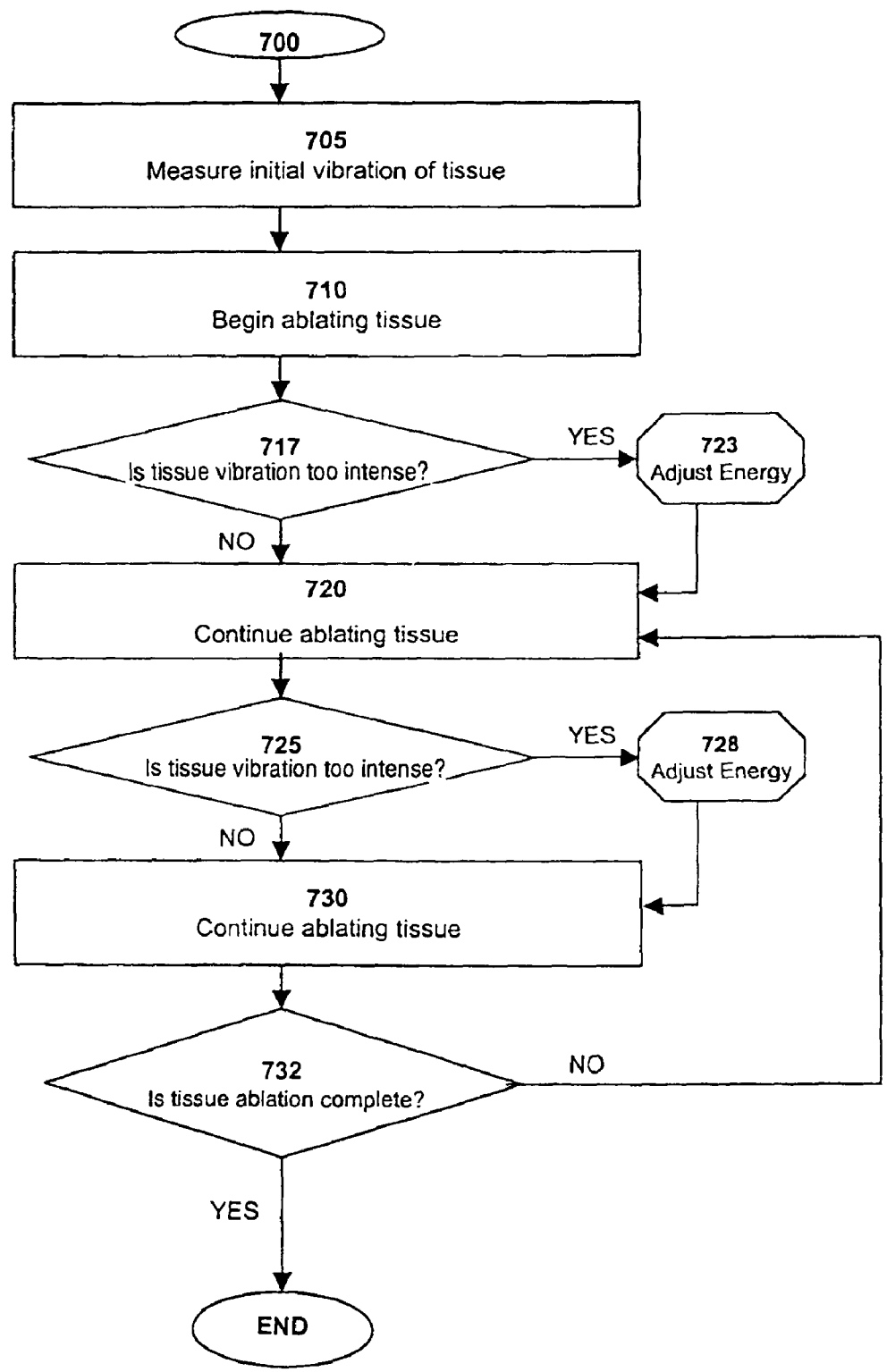
FIG. 7 shows a flow diagram of one embodiment of the present invention.

FIG. 7 shows a flow diagram of one embodiment of the present invention. The patient is prepared for an ablation procedure at 700. Once the patient is prepared, the initial state of tissue vibration is measured (Block 705). The initial state of tissue vibration is then used as a gauge to compare with the state of tissue vibration during the procedure. At this point, ablation of the target tissue is begun (Block 710). Tissue vibration is then monitored (Blocks 717 and 725). If the tissue vibration becomes to intense, the energy supplied to ablation apparatus 20 is modified or adjusted (Blocks 723 and 728).

Figure 8:
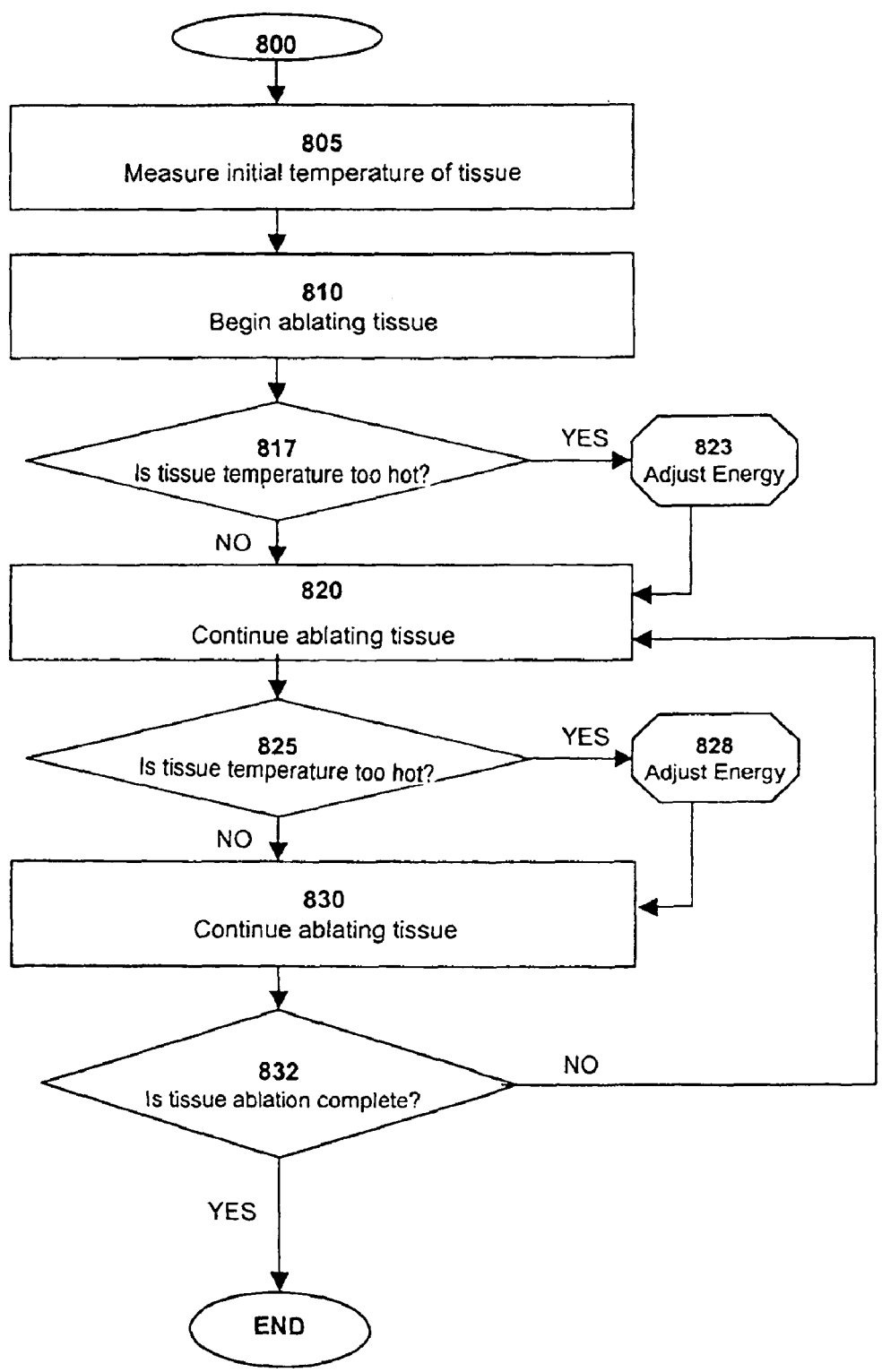
FIG. 8 shows a flow diagram of another embodiment of the present invention.

FIG. 8 shows a flow diagram of another embodiment of the present invention. The patient is prepared for an ablation procedure at 800. Once the patient is prepared, the initial state of tissue temperature is measured (Block 805). The initial state of tissue temperature is then used as a gauge to compare with the state of tissue temperature during the procedure. At this point, ablation of the target tissue is begun (Block 810). Tissue temperature is then monitored (Blocks 817 and 825). If the tissue temperature becomes to hot, the energy supplied to ablation apparatus 20 is modified or adjusted (Blocks 823 and 828).

Irrigation source 40, as discussed above, may be any suitable source of irrigation fluid. Irrigation source 40 may include a manual or electric pump, an infusion pump, a syringe pump, a syringe, a pressurized reservoir or bag, a squeeze bulb or other fluid moving means, device or system. For example, a pump may be connected to power source 30 or it may have its own source of power. Irrigation source 40 may be powered by AC current, DC current, or it may be battery powered either by a disposable or re-chargeable battery. Irrigation source 40 may comprise one or more fluid regulators, e.g., to control fluid flow rate, valves, fluid reservoirs, conduits, lines, tubes and/or hoses. The conduits, lines, tubes, or hoses may be flexible or rigid. For example, a flexible line may be used to communicate fluid to ablation apparatus 20, thereby allowing ablation apparatus 20 to be easily manipulated by a surgeon. Fluid reservoirs, for example, may be an IV bag or bottle. It is preferred that the irrigation fluid be sterile.

Irrigation source 40 may be incorporated into ablation apparatus 20, thereby delivering irrigation fluid at the ablation site. Irrigation source 40 may be slaved to ablation apparatus 20, output device 25, generator 80 and/or sensor 24. For example, irrigation source 40 may be designed to automatically stop or start the delivery of irrigation fluid during ablation of tissue. Irrigation source 40 may be slaved to a robotic system or a robotic system may be slaved to irrigation source 40.

Irrigation source 40 may comprise a surgeon-controlled switch. For example, a switch may be incorporated in or on irrigation source 40 or any other location easily and quickly accessed by the surgeon for regulation of irrigation fluid delivery by the surgeon. The switch may be, for example, a hand switch, a foot switch, or a voice-activated switch comprising voice-recognition technologies.

Irrigation source 40 may include a visual and/or audible signal used to alert a surgeon to any change in the delivery of irrigation fluid. For example, a beeping tone or flashing light may be used to alert the surgeon that a change has occurred in the delivery of irrigation fluid.

As discussed earlier, an irrigation fluid may include saline, e.g., normal, hypotonic or hypertonic saline, Ringer's solution, ionic contrast, blood, or other energy-conducting liquids. An ionic irrigation fluid electrically couples the one or more electrodes of ablation apparatus 20 to the tissue to be ablated thereby lowering the impedance at the ablation site. An ionic irrigating fluid may create a larger effective electrode surface. An irrigating fluid may cool the surface of the tissue thereby preventing the overheating or cooking of tissue which can cause popping, desiccation, and charring of tissue. A hypotonic irrigating fluid may be used to electrically insulate a region of tissue thereby preventing ablation of tissue by an electrical means.

Diagnostic or therapeutic agents, such as one or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand) may be delivered before, with or after the delivery of the irrigating fluid. Biological agents may be found in nature (naturally occurring) or may be chemically synthesized. Cells and cell components, e.g., mammalian cells, may be delivered before, with or after the delivery of the irrigating fluid.

Generator 80 may comprise a control unit and power source 30. Ablation apparatus 20 may be permanently or removably attached to a source of energy such as electrical, radiofrequency (RF), laser, thermal, microwave or ultrasound or any other appropriate type of energy that may be used to ablate tissue. Generator 80 may be powered by AC current, DC current or it may be battery powered either by a disposable or re-chargeable battery. Generator 80 may be used to coordinate the various elements of system 10. For example, generator 80 may be configured to synchronize activation and deactivation of irrigation source 40 with ablation or irrigation source 40 may be incorporated into generator 80.

Generator 80 may incorporate a controller as described above or any suitable processor. For example, the processor may process sensed information from sensor 24. The controller may store and/or process such information before, during and/or after an ablation procedure. For example, the patient's tissue temperature may be sensed, stored and processed prior to and during the ablation procedure.

Generator 80 may be used to control the power levels of ablation apparatus 20. Generator 80 may also gather and process information from sensor 24. This information may be used to adjust power levels and ablation times. Generator 80 may incorporate one or more switches to facilitate regulation of the various system components by the surgeon. One example of such a switch is a foot pedal. The switch may also be, for example, a hand switch, or a voice-activated switch comprising voice-recognition technologies. The switch may be incorporated in or on one of the surgeon's instruments, such as surgical site retractor, e.g., a sternal or rib retractor, or ablation apparatus 20, or any other location easily and quickly accessed by the surgeon. Generator 80 may also include a display. Generator 80 may also include other means of indicating the status of various components to the surgeon such as a numerical display, gauges, a monitor display or audio feedback.

Generator 80 may also incorporate a cardiac stimulator and/or cardiac monitor. For example, electrodes used to stimulate or monitor the heart may or may not be incorporated into ablation apparatus 20. Generator 80 may comprise a surgeon-controlled switch for cardiac stimulation or monitoring, as discussed earlier. For example, a switch may be incorporated in or on generator 80 or any other location easily and quickly accessed by the surgeon for regulation of generator 80 by the surgeon. The switch may be, for example, a hand switch, a foot switch, or a voice-activated switch comprising voice-recognition technologies.

A visual and/or audible signal used to alert a surgeon to the completion or resumption of ablation, suction, sensing, monitoring, stimulation and/or delivery of irrigation fluid, drugs and/or cells may be incorporated into generator 80. For example, a beeping tone or flashing light that increases in frequency as the ablation period ends or begins may be used.

System 10, ablation apparatus 20, or sensor device 524 may comprise one or more additional sensors besides a vibration sensor 24. For example, ablation system 10, apparatus 20, or sensor device 524 may comprise one or more temperature-sensitive elements, such as a thermocouple, to allow a surgeon to monitor temperature changes of a patient's tissue. For example, FIGS. 5 and 6 show two different embodiments of sensor device 524 comprising a vibration sensor 24 and a plurality of temperature-sensitive elements 534 positioned along support surface 544. Alternatively, system 10, ablation apparatus 20, or sensor device 524 may comprise one or more sensors to sense and/or monitor voltage, amperage, wattage and/or impedance.

Alternatively, system 10, ablation apparatus 20, or sensor device 524 may comprise one or more blood gas sensors for measuring the concentration or saturation of a gas in the blood stream. For example, system 10, ablation apparatus 20, or sensor device 524 may comprise a sensor for measuring the concentration or saturation of oxygen or carbon dioxide in the blood. Alternatively, system 10, ablation apparatus 20, or sensor device 524 may comprise one or more suitable sensors for measuring blood pressure or flow, for example a Doppler ultrasound sensor system, or a sensor for measuring hematocrit (HCT) levels.

Alternatively, system 10, ablation apparatus 20, or sensor device 524 may comprise one or more biosensors, for example, comprising an immobilized biocatalyst, enzyme, immunoglobulin, bacterial, mammalian or plant tissue, cell and/or subcellular fraction of a cell. For example, the tip of a biosensor may comprise a mitochondrial fraction of a cell, thereby providing the sensor with a specific biocatalytic activity.

System 10, ablation apparatus 20, or sensor device 524 may comprise one or more sensors based on potentiometric technology or fiber optic technology. For example, the sensor may comprise a potentiometric or fiber optic transducer. An optical sensor may be based on either an absorbance or fluorescence measurement and may include an UV, a visible or an IR light source.

System 10, ablation apparatus 20, or sensor device 524 may comprise one or more sensors used to detect naturally detectable properties representative of one or more characteristics, e.g., chemical, physical or physiological, of a patient's bodily tissues or fluids. For example, naturally detectable properties of patient's bodily tissues or fluids may include pH, fluid flow, electrical current, impedance, temperature, pressure, components of metabolic processes, chemical concentrations, for example, the absence or presence of specific peptides, proteins, enzymes, gases, ions, etc.

System 10, ablation apparatus 20, or sensor device 524 may comprise one or more imaging systems, camera systems operating in UV, visible, or IR range; electrical sensors; voltage sensors; current sensors; piezoelectric sensors; electromagnetic interference (EMI) sensors; photographic plates, polymer-metal sensors; charge-coupled devices (CCDs); photo diode arrays; chemical sensors, electrochemical sensors; pressure sensors, sound wave sensors; magnetic sensors; UV light sensors; visible light sensors; IR light sensors; radiation sensors; flow sensors; temperature sensors; vacuum sensors; or any other appropriate or suitable sensor.

Sensors may be incorporated into ablation apparatus 20 or they may be placed or used at a location differing from the location of ablation apparatus 20. For example, sensors may be placed in contact with the inside surface of a patient's heart while ablation apparatus 20 is placed or used on the outside surface of the patient's heart.

Ablation apparatus 20, irrigation source 40 and/or generator 80 may be slaved to one or more sensors. For example, ablation apparatus 20 and/or generator 80 may be designed to automatically stop ablation if a sensor measures a predetermined sensor value, e.g., a particular temperature value. In one embodiment of the invention, if a sensor of the present invention indicates that ablated tissue has reached a particular temperature, ablation is stopped automatically, thereby preventing charring of the tissue. Suction may also be slaved to one or more sensors.

One or more sensors of the present invention may include a visual and/or audible signal used to alert a surgeon to any change in the one or more characteristics the sensor is monitoring. For example, a beeping tone or flashing light that increases in frequency as tissue temperature rises may be used to alert the surgeon.

Ablation apparatus 20, output device 25, irrigation source 40, generator 80, sensor device 524, and/or sensor 24 may be slaved to a robotic system or a robotic system may be slaved to ablation apparatus 20, output device 25, irrigation source 40, generator 80, sensor device 524, and/or sensor 24. Additional sensors and/or a suction source may also be slaved to a robotic system or a robotic system may be slaved to the additional sensors and/or the suction source. Computer- and voice-controlled robotic systems that position and maneuver endoscopes and/or other surgical instruments for performing microsurgical procedures through small incisions may be used by the surgeon to perform precise and delicate maneuvers: These robotic systems may allow the surgeon to perform a variety of microsurgical procedures including tissue ablation. In general, robotic systems may include head-mounted displays which integrate 3-D visualization of surgical anatomy and related diagnostic and monitoring data, miniature high resolution 2-D and 3-D digital cameras, a computer, a high power light source and a standard video monitor.

One or more of a variety of pharmacological agents or drugs may be delivered or administered to an ablation patient, for a variety of functions and purposes as described below, prior to an ablation procedure, intermittently during an ablation procedure, continuously during an ablation procedure and/or following an ablation procedure. For example, one or more of a variety of pharmacological agents or drugs, as discussed below, may be delivered before, with or after the delivery of the irrigating fluid, as discussed earlier.

Drugs, drug formulations or compositions suitable for administration to an ablation patient may include a pharmaceutically acceptable carrier or solution in an appropriate dosage. There are a number of pharmaceutically acceptable carriers that may be used for delivery of various drugs, for example, via direct injection, oral delivery, suppository delivery, transdermal delivery, epicardial delivery and/or inhalation delivery. Pharmaceutically acceptable carriers include a number of solutions, preferably sterile, for example, water, saline, Ringer's solution and/or sugar solutions such as dextrose in water or saline. Other possible carriers that may be used include sodium citrate, citric acid, amino acids, lactate, mannitol, maltose, glycerol, sucrose, ammonium chloride, sodium chloride, potassium chloride, calcium chloride, sodium lactate, and/or sodium bicarbonate. Carrier solutions may or may not be buffered.

Drug formulations or compositions may include antioxidants or preservatives such as ascorbic acid. They may also be in a pharmaceutically acceptable form for parenteral administration, for example to the cardiovascular system, or directly to the heart, such as intracoronary infusion or injection. Drug formulations or compositions may comprise agents that provide a synergistic effect when administered together. A synergistic effect between two or more drugs or agents may reduce the amount that normally is required for therapeutic delivery of an individual drug or agent. Two or more drugs may be administered, for example, sequentially or simultaneously. Drugs may be administered via one or more bolus injections and/or infusions or combinations thereof. The injections and/or infusions may be continuous or intermittent. Drugs may be administered, for example, systemically or locally, for example, to the heart, to a coronary artery and/or vein, to a pulmonary artery and/or vein, to the right atrium and/or ventricle, to the left atrium and/or ventricle, to the aorta, to the AV node, to the SA node, to a nerve and/or to the coronary sinus. Drugs may be administered or delivered via intravenous, intracoronary and/or intraventricular administration in a suitable carrier. Examples of arteries that may be used to deliver drugs to the AV node include the AV node artery, the right coronary artery, the right descending coronary artery, the left coronary artery, the left anterior descending coronary artery and Kugel's artery. Drugs may be delivered systemically, for example, via oral, transdermal, intranasal, suppository or inhalation methods. Drugs also may be delivered via a pill, a spray, a cream, an ointment or a medicament formulation.

In one embodiment of the present invention, system 10 may include a drug delivery device (not shown). The drug delivery device may comprise a catheter, such as a drug delivery catheter or a guide catheter, a patch, such as a transepicardial patch that slowly releases drugs directly into the myocardium, a cannula, a pump and/or a hypodermic needle and syringe assembly. A drug delivery catheter may include an expandable member, e.g., a low-pressure balloon, and a shaft having a distal portion, wherein the expandable member is disposed along the distal portion. A catheter for drug delivery may comprise one or more lumens and may be delivered endovascularly via insertion into a blood vessel, e.g., an artery such as a femoral, radial, subclavian or coronary artery. The catheter can be guided into a desired position using various guidance techniques, e.g., flouroscopic guidance and/or a guiding catheter or guide wire techniques. Drugs may be delivered via an iontophoretic drug delivery device placed on the heart. In general, the delivery of ionized drugs may be enhanced via a small current applied across two electrodes. Positive ions may be introduced into the tissues from the positive pole, or negative ions from the negative pole. The use of iontophoresis may markedly facilitate the transport of certain ionized drug molecules. For example, lidocaine hydrochloride may be applied to the heart via a drug patch comprising the drug. A positive electrode could be placed over the patch and current passed. The negative electrode would contact the heart or other body part at some desired distance point to complete the circuit. One or more of the iontophoresis electrodes may also be used as nerve stimulation electrodes or as cardiac stimulation electrodes.

A drug delivery device may be incorporated into ablation apparatus 20 thereby delivering drugs at or adjacent the ablation site or the drug delivery device may be placed or used at a location differing from the location of ablation apparatus 20. For example, a drug delivery device may be placed in contact with the inside surface of a patient's heart while ablation apparatus 20 is placed or used on the outside surface of the patient's heart.

The drug delivery device may be slaved to ablation apparatus 20, output device 25, generator 80 and/or sensor 24. For example, a drug delivery device may be designed to automatically stop or start the delivery of drugs during ablation of tissue. The drug delivery device may be slaved to a robotic system or a robotic system may be slaved to the drug delivery device.

The drug delivery device may comprise a surgeon controlled switch. For example, a switch may be incorporated in or on the drug delivery device or any other location easily and quickly accessed by the surgeon for regulation of drug delivery by the surgeon. The switch may be, for example, a hand switch, a foot switch, or a voice-activated switch comprising voice-recognition technologies.

The drug delivery device may include a visual and/or audible signal used to alert a surgeon to any change in the delivery of drugs. For example, a beeping tone or flashing light that increases in frequency as the rate of drug delivery increases may be used to alert the surgeon.

The two divisions of the autonomic nervous system that regulate the heart have opposite functions. First, the adrenergic or sympathetic nervous system increases heart rate by releasing epinephrine and norepinephrine. Second, the parasympathetic system also known as the cholinergic nervous system or the vagal nervous system decreases heart rate by releasing acetylcholine. Catecholamines such as norepinephrine (also called noradrenaline) and epinephrine (also called adrenaline) are agonists for beta-adrenergic receptors. An agonist is a stimulant biomolecule or agent that binds to a receptor.

Beta-adrenergic receptor blocking agents compete with beta-adrenergic receptor stimulating agents for available beta-receptor sites. When access to beta-receptor sites are blocked by receptor blocking agents, also known as beta-adrenergic blockade, the chronotropic or heart rate, inotropic or contractility, and vasodilator responses to receptor stimulating agents are decreased proportionately. Therefore, beta-adrenergic receptor blocking agents are agents that are capable of blocking beta-adrenergic receptor sites.

Since beta-adrenergic receptors are concerned with contractility and heart rate, stimulation of beta-adrenergic receptors, in general, increases heart rate, the contractility of the heart and the rate of conduction of electrical impulses through the AV node and the conduction system.

Drugs, drug formulations and/or drug compositions that may be used according to this invention may include any naturally occurring or chemically synthesized (synthetic analogues) beta-adrenergic receptor blocking agents. Beta-adrenergic receptor blocking agents or β-adrenergic blocking agents are also known as beta-blockers or β-blockers and as class II antiarrhythmics.

The term "beta-blocker" appearing herein may refer to one or more agents that antagonize the effects of beta-stimulating catecholamines by blocking the catecholamines from binding to the beta-receptors. Examples of beta-blockers include, but are not limited to, acebutolol, alprenolol, atenolol, betantolol, betaxolol, bevantolol, bisoprolol, carterolol, celiprolol, chlorthalidone, esmolol, labetalol, metoprolol, nadolol, penbutolol, pindolol, propranolol, oxprenolol, sotalol, teratolo, timolol and combinations, mixtures and/or salts thereof.

The effects of administered beta-blockers may be reversed by administration of beta-receptor agonists, e.g., dobutamine or isoproterenol.

The parasympathetic or cholinergic system participates in control of heart rate via the sinoatrial (SA) node, where it reduces heart rate. Other cholinergic effects include inhibition of the AV node and an inhibitory effect on contractile force. The cholinergic system acts through the vagal nerve to release acetylcholine, which, in turn, stimulates cholinergic receptors. Cholinergic receptors are also known as muscarinic receptors. Stimulation of the cholinergic receptors decreases the formation of cAMP. Stimulation of cholinergic receptors generally has an opposite effect on heart rate compared to stimulation of beta-adrenergic receptors. For example, beta-adrenergic stimulation increases heart rate, whereas cholinergic stimulation decreases it. When vagal tone is high and adrenergic tone is low, there is a marked slowing of the heart (sinus bradycardia). Acetylcholine effectively reduces the amplitude, rate of increase and duration of the SA node action potential. During vagal nerve stimulation, the SA node does not arrest. Rather, pacemaker function may shift to cells that fire at a slower rate. In addition, acetylcholine may help open certain potassium channels thereby creating an outward flow of potassium ions and hyperpolarization. Acetylcholine also slows conduction through the AV node.

Drugs, drug formulations and/or drug compositions that may be used according to this invention may include any naturally occurring or chemically synthesized (synthetic analogues) cholinergic agent. The term "cholinergic agent" appearing herein may refer to one or more cholinergic receptor modulators or agonists. Examples of cholinergic agents include, but are not limited to, acetylcholine, carbachol (carbamyl choline chloride), bethanechol, methacholine, arecoline, norarecoline and combinations, mixtures and/or salts thereof.

Drugs, drug formulations and/or drug compositions that may be used according to this invention may include any naturally occurring or chemically synthesized cholinesterase inhibitor. The term "cholinesterase inhibitor" appearing herein may refer to one or more agents that prolong the action of acetylcholine by inhibiting its destruction or hydrolysis by cholinesterase. Cholinesterase inhibitors are also known as acetylcholinesterase inhibitors. Examples of cholinesterase inhibitors include, but are not limited to, edrophonium, neostigmine, neostigmine methylsulfate, pyridostigmine, tacrine and combinations, mixtures and/or salts thereof.

There are ion-selective channels within certain cell membranes. These ion selective channels include calcium channels, sodium channels and/or potassium channels. Therefore, other drugs, drug formulations and/or drug compositions that may be used according to this invention may include any naturally occurring or chemically synthesized calcium channel blocker. Calcium channel blockers inhibit the inward flux of calcium ions across cell membranes of arterial smooth muscle cells and myocardial cells. Therefore, the term "calcium channel blocker" appearing herein may refer to one or more agents that inhibit or block the flow of calcium ions across a cell membrane. The calcium channel is generally concerned with the triggering of the contractile cycle. Calcium channel blockers are also known as calcium ion influx inhibitors, slow channel blockers, calcium ion antagonists, calcium channel antagonist drugs and as class IV antiarrhythmics. A commonly used calcium channel blocker is verapamil.

Administration of a calcium channel blocker, e.g., verapamil, generally prolongs the effective refractory period within the AV node and slows AV conduction in a rate-related manner, since the electrical activity through the AV node depends significantly upon the influx of calcium ions through the slow channel. A calcium channel blocker has the ability to slow a patient's heart rate, as well as produce AV block. Examples of calcium channel blockers include, but are not limited to, amiloride, amlodipine, bepridil, diltiazem, felodipine, isradipine, mibefradil, nicardipine, nifedipine (dihydropyridines), nickel, nimodinpine, nisoldipine, nitric oxide (NO), norverapamil and verapamil and combinations, mixtures and/or salts thereof. Verapamil and diltiazem are very effective at inhibiting the AV node, whereas drugs of the nifedipine family have a lesser inhibitory effect on the AV node. Nitric oxide (NO) indirectly promotes calcium channel closure. NO may be used to inhibit contraction. NO may also be used to inhibit sympathetic outflow, lessen the release of norepinephrine, cause vasodilation, decrease heart rate and decrease contractility. In the SA node, cholinergic stimulation leads to formation of NO.

Other drugs, drug formulations and/or drug compositions that may be used according to this invention may include any naturally occurring or chemically synthesized sodium channel blocker. Sodium channel blockers are also known as sodium channel inhibitors, sodium channel blocking agents, rapid channel blockers or rapid channel inhibitors. Antiarrhythmic agents that inhibit or block the sodium channel are known as class I antiarrhythmics, examples include, but are not limited to, quinidine and quinidine-like agents, lidocaine and lidocaine-like agents, tetrodotoxin, encainide, flecainide and combinations, mixtures and/or salts thereof. Therefore, the term "sodium channel blocker" appearing herein may refer to one or more agents that inhibit or block the flow of sodium ions across a cell membrane or remove the potential difference across a cell membrane. For example, the sodium channel may also be totally inhibited by increasing the extracellular potassium levels to depolarizing hyperkalemic values, which remove the potential difference across the cell membrane. The result is inhibition of cardiac contraction with cardiac arrest (cardioplegia). The opening of the sodium channel (influx of sodium) is for swift conduction of the electrical impulse throughout the heart.

Other drugs, drug formulations and/or drug compositions that may be used according to this invention may include any naturally occurring or chemically synthesized potassium channel agent. The term "potassium channel agent" appearing herein may refer to one or more agents that impact the flow of potassium ions across the cell membrane. There are two major types of potassium channels. The first type of channel is voltage-gated and the second type is ligand-gated. Acetylcholine-activated potassium channels, which are ligand-gated channels, open in response to vagal stimulation and the release of acetylcholine. Opening of the potassium channel causes hyperpolarization, which decreases the rate at which the activation threshold is reached. Adenosine is one example of a potassium channel opener. Adenosine slows conduction through the AV node. Adenosine, a breakdown product of adenosine triphosphate, inhibits the AV node and atria. In atrial tissue, adenosine causes the shortening of the action potential duration and causes hyperpolarization. In the AV node, adenosine has similar effects and also decreases the action potential amplitude and the rate of increase of the action potential. Adenosine is also a direct vasodilator by its actions on the adenosine receptor on vascular smooth muscle cells. In addition, adenosine acts as a negative neuromodulator, thereby inhibiting release of norepinephrine. Class III antiarrhythmic agents also known as potassium channel inhibitors lengthen the action potential duration and refractoriness by blocking the outward potassium channel to prolong the action potential. Amiodarone and d-sotalol are both examples of class III antiarrhythmic agents.

Potassium is the most common component in cardioplegic solutions. High extracellular potassium levels reduce the membrane resting potential. Opening of the sodium channel, which normally allows rapid sodium influx during the upstroke of the action potential, is therefore inactivated because of a reduction in the membrane resting potential.

Drugs, drug formulations and/or drug compositions that may be used according to this invention may comprise one or more of any naturally occurring or chemically synthesized beta-blocker, cholinergic agent, cholinesterase inhibitor, calcium channel blocker, sodium channel blocker, potassium channel agent, adenosine, adenosine receptor agonist, adenosine deaminase inhibitor, dipyridamole, monoamine oxidase inhibitor, digoxin, digitalis, lignocaine, bradykinin agents, serotoninergic agonist, antiarrythmic agents, cardiac glycosides, local anesthetics and combinations or mixtures thereof. Digitalis and digoxin both inhibit the sodium pump. Digitalis is a natural inotrope derived from plant material, while digoxin is a synthesized inotrope. Dipyridamole inhibits adenosine deaminase, which breaks down adenosine. Drugs, drug formulations and/or drug compositions capable of reversibly suppressing autonomous electrical conduction at the SA and/or AV node, while still allowing the heart to be electrically paced to maintain cardiac output may be used according to this invention.

Beta-adrenergic stimulation or administration of calcium solutions may be used to reverse the effects of a calcium channel blocker such as verapamil. Agents that promote heart rate and/or contraction may be used in the present invention. For example, dopamine, a natural catecholamine, is known to increase contractility. Positive inotropes are agents that specifically increase the force of contraction of the heart. Glucagon, a naturally occurring hormone, is known to increase heart rate and contractility. Glucagon may be used to reverse the effects of a beta-blocker since its effects bypass the beta receptor. Forskolin is known to increase heart rate and contractility. As mentioned earlier, epinephrine and norepinephrine naturally increase heart rate and contractility. Thyroid hormone, phosphodiesterase inhibitors and prostacyclin, a prostaglandin, are also known to increase heart rate and contractility. In addition, methylxanthines are known to prevent adenosine from interacting with its cell receptors.

One or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand) may be delivered or administered to an ablation patient prior to an ablation procedure, intermittently during an ablation procedure, continuously during an ablation procedure and/or following an ablation procedure. Biological agents may be found in nature (naturally occurring) or may be chemically synthesized.

The ablation procedure may be non-invasive, minimally invasive and/or invasive. The ablation procedure may entail a port-access approach, a partially or totally endoscopic approach, a sternotomy approach or a thoracotomy approach. The ablation procedure may include the use of various mechanical stabilization devices or techniques as well as various robotic or imaging systems. For example, mechanical stabilization and manipulation devices are described in U.S. Pat. Nos. 5,836,311; 5,927,284 and 6,015,378, and co-assigned U.S. patent applications Ser. No. 09/396,047, filed Sep. 15, 1999, Ser. No. 09/559,785, filed Apr. 27, 2000, and Ser. No. 09/678,203, filed Oct. 2, 2000; and European Patent Publication No. EP 0 993 806. These patents and applications are assigned to Medtronic, Inc. and are incorporated herein by reference.

In one method of the present invention, the heart may be temporarily slowed or intermittently stopped for short periods of time to permit the surgeon to accomplish a required surgical task and yet still allow the heart itself to supply blood circulation to the body. For example, stimulation of the vagus nerve in order to temporarily and intermittently slow or stop the heart is described in U.S. Pat. No. 6,006,134 entitled "Method and Device for Electronically Controlling the Beating of a Heart Using Venous Electrical Stimulation of Nerve Fibers", Dec. 21, 1999, to Hill and Junkman. This patent is assigned to Medtronic, Inc. and is incorporated herein by reference.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A method of ablating organic tissue, comprising:
sensing an initial state of vibration of the organic tissue prior to ablating the organic tissue;
positioning an electrode adjacent the organic tissue;
supplying electrical power to the electrode to effect ablation of the organic tissue;
sensing with a sensor positioned adjacent the electrode the vibration of the organic tissue being ablated wherein the vibration is self-generated in the organic tissue in response to the ablation and the self-generated vibration occurs during phase-transition but prior to boiling of water in the organic tissue;
determining a difference in vibration between the initial state of vibration and the self-generated vibration; and
reducing power to the electrode when the self-generated vibration reaches a given value.

2. The method of claim 1, further comprising:
halting the power when the self-generated vibration reaches a given value.

3. The method of claim 1, further comprising:
supplying fluid from a fluid supply to the tissue; and
halting the fluid supply when the self-generated vibration reaches a given value.

4. The method of claim 1 further comprising:
sending a signal from the sensor to a switch to reduce the power.

5. The method of claim 1, further comprising:
providing output from an output device when the self-generated vibration reaches a given value.

6. The method of claim 5 further comprising:
sending a signal from the sensor to the output device; and
sending an indicator signal from the output device.

7. The method of claim 1 wherein the sensor is a piezoelectric crystal.

8. The method of claim 1 wherein the sensor is a piezoelectric polymer.

9. The method of claim 1 wherein the sensor is integrated with the electrode.

* * * * *